United States Patent
Ryu et al.

(10) Patent No.: US 8,160,700 B1
(45) Date of Patent: Apr. 17, 2012

(54) ADAPTIVE SINGLE SITE AND MULTI-SITE VENTRICULAR PACING

(75) Inventors: Kyungmoo Ryu, Palmdale, CA (US); Jong Gill, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 1348 days.

(21) Appl. No.: 11/749,674

(22) Filed: May 16, 2007

(51) Int. Cl.
*A61N 1/362* (2006.01)
*A61N 1/365* (2006.01)

(52) U.S. Cl. ............................................. 607/9; 607/25

(58) Field of Classification Search ................ 607/9, 27
See application file for complete search history.

(56) References Cited

U.S. PATENT DOCUMENTS

| | | | |
|---|---|---|---|
| 4,712,555 | A | 12/1987 | Thornander et al. |
| 4,788,980 | A | 12/1988 | Mann et al. |
| 4,940,052 | A | 7/1990 | Mann et al. |
| 4,944,298 | A | 7/1990 | Sholder |
| 5,466,254 | A | 11/1995 | Helland |
| 5,476,483 | A | 12/1995 | Bornzin et al. |
| 6,314,323 | B1 | 11/2001 | Ekwall |
| 6,978,184 | B1 | 12/2005 | Marcus et al. |
| 2002/0143264 | A1 | 10/2002 | Ding et al. |
| 2002/0169484 | A1* | 11/2002 | Mathis et al. ..................... 607/9 |
| 2003/0014084 | A1 | 1/2003 | VanHout |
| 2004/0215252 | A1* | 10/2004 | Verbeek et al. ..................... 607/9 |
| 2005/0125041 | A1* | 6/2005 | Min et al. ........................... 607/9 |
| 2006/0020294 | A1* | 1/2006 | Brockway et al. .............. 607/17 |
| 2008/0065166 | A1* | 3/2008 | Sathaye et al. .................. 607/28 |
| 2008/0177344 | A1 | 7/2008 | Maskara et al. |
| 2008/0306567 | A1* | 12/2008 | Park et al. ....................... 607/27 |

OTHER PUBLICATIONS

Ryu, K., et al, Comparative effects of single- and linear triple-site rapid bipolar pacing on atrial activation in canine models; Am J Physiol Heat Circ Physiol 289: H374-H384, 2005.
NonFinal Office Action, mailed Jul. 7, 2009—Related U.S. Appl. No. 11/749,662.
Final Office Action, mailed Mar. 24, 2010—Related U.S. Appl. No. 11/749,662.
Advisory Action, mailed Jun. 16, 2010—Related U.S. Appl. No. 11/749,662.

* cited by examiner

*Primary Examiner* — Carl H. Layno
*Assistant Examiner* — Jon-Eric C. Morales

(57) ABSTRACT

An exemplary method includes delivering a cardiac pacing therapy using an electrode configuration for left ventricular, single site pacing or left ventricular, multi-site pacing, measuring a series of interventricular conduction delays using the left ventricular pacing and right ventricular sensing (IVCD-LR), comparing the interventricular conduction delay values to a limit and, based on the comparison, deciding whether to change the electrode configuration for the left ventricular pacing. Other exemplary methods, devices, systems, etc., are also disclosed.

23 Claims, 18 Drawing Sheets

EXEMPLARY METHOD 700

CRITERIA FOR $LV_{P2}$ 750

BEAT-TO-BEAT: IVCD-LR OR IVCD-RL > $\Delta T_{OPT}$ + $T^+$ MS ?

BEAT-TO-BEAT: IVCD-LR OR IVCD-RL > $\Delta T_{OPT}$ − $T^-$ MS ?

MOVING AVERAGE: AVE. IVCD-LR OR AVE. IVCD-RL > $\Delta T_{OPT}$ + X MS ?

OTHER STATISTICAL TECHNIQUES

EXEMPLARY METHODS 1700

Exemplary Equations for Atrial and/or Ventricular Pacing 1800

States 1810

$AS_0$ = Base State (e.g., Rest)
$AS_1$ = Active State 1
$AS_2$ = Active State 2
$AS_N$ = Active State N

PV or AV States 1820

$\beta = \delta/DD(AS_0)$
$\beta = \delta/AD(AS_0)$ $\delta = f(\Delta P(AS_0))$  $\delta = f(\Delta A(AS_0))$
$\delta = f(\Delta P(AS_x))$  $\delta = f(\Delta A(AS_x))$ $PV(AS_0) = \Delta P(AS_0) + \delta$
$AV(AS_0) = \Delta A(AS_0) + \delta$ $PV(AS_x) = \Delta P(AS_x) + \beta*DD(AS_x)$
$AV(AS_x) = \Delta A(AS_x) + \beta*AD(AS_x)$

VV States 1830

$\alpha$ = Constant
$\alpha = \alpha(AS_0)$
$\alpha = \alpha(AS_x)$ $\Delta(AS_0) = R_{LV}(AS_0) - R_{RV}(AS_0)$
$\Delta(AS_x) = R_{LV}(AS_x) - R_{RV}(AS_x)$ $\Delta_{IVCD}(AS_0) = IVCD\text{-}LR(AS_0) - IVCD\text{-}RL(AS_0)$
$\Delta_{IVCD}(AS_x) = IVCD\text{-}LR(AS_x) - IVCD\text{-}RL(AS_x)$ $VV(AS_0) = \alpha*(\Delta(AS_0) + \Delta_{IVCD}(AS_0))$
$VV(AS_x) = \alpha*(\Delta(AS_x) + \Delta_{IVCD}(AS_x))$

Fig. 18

ADAPTIVE SINGLE SITE AND MULTI-SITE VENTRICULAR PACING

RELATED APPLICATIONS

This application is related to U.S. patent application Ser. No. 11/749,662, filed May 16, 2007 entitled "Adaptive Single Site and Multi-Site Ventricular Pacing".

TECHNICAL FIELD

Subject matter presented herein generally relates to cardiac pacing therapy and, in particular, to optimizing ventricular pacing

BACKGROUND

Left ventricular cardiac pacing therapies generally rely implanting a lead in a venous structure of the left ventricle and stimulating the left ventricle using a single electrode or a bipolar pair of electrodes of the lead. Such pacing is referred to herein as "single site" pacing. More specifically, where a single electrode is used, the electrode configuration is known as a unipolar electrode configuration while where a bipolar electrode pair is used (usually a closely spaced pair), the electrode configuration is known as a bipolar electrode configuration. In either instance, these electrode configurations are considered single site and, hence, pacing that uses one of these electrode configurations is considered single site pacing.

While single site pacing has proven beneficial, multi-site pacing may, in some instances, be more beneficial. For example, a study by Ryu et al. ("Comparative effects of single- and linear triple-site rapid bipolar pacing on atrial activation in canine models", *Am J Physiol Heat Circ Physiol* 289: H374-H384, 2005) tested the hypothesis that in the canine right atrium, bipolar, linear, triple-site rapid pacing creates more uniform propagation than bipolar, single-site rapid pacing and thereby minimizes or eliminates conduction block or delay (potential proarrhythmic effects that might otherwise be present due to rapid pacing). The study showed that, at rapid atrial pacing rates, both parallel and perpendicular linear triple-site pacing created more uniform linear impulse propagation and that single-site pacing created heterogeneous propagation in the presence of conduction abnormalities.

While multi-site pacing may be beneficial, multi-site pacing may require more energy when compared to single site pacing. Further, selection of multiple sites can be a more complex task compared to selection of a single site. As described herein, various exemplary techniques facilitate site selection and site optimization for right ventricular pacing, left ventricular pacing and/or bi-ventricular pacing. Various exemplary techniques can automatically optimize cardiac therapy using single site and/or multi-site pacing.

SUMMARY

An exemplary method includes delivering a cardiac pacing therapy using an electrode configuration for left ventricular, single site pacing or left ventricular, multi-site pacing, measuring a series of interventricular conduction delays using the left ventricular pacing and right ventricular sensing (IVCD-LR), comparing the interventricular conduction delay values to a limit and, based on the comparison, deciding whether to change the electrode configuration for the left ventricular pacing. Other exemplary methods, devices, systems, etc., are also disclosed. In general, the various methods, devices, systems, etc., described herein, and equivalents thereof, are suitable for use in a variety of pacing therapies and/or other cardiac related therapies.

BRIEF DESCRIPTION OF THE DRAWINGS

Features and advantages of the described implementations can be more readily understood by reference to the following description taken in conjunction with the accompanying drawings.

FIG. 18 is a series of equations that may be used for atrial and/or ventricular pacing, including bi-ventricular pacing.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are used at times to reference like parts or elements throughout the description.

Overview

Exemplary methods, devices, systems, etc., pertain generally to ventricular pacing. For example, various exemplary methods include measuring a series of conduction delays at the time of implant of a ventricular pacing lead and selecting an optimal electrode configuration for ventricular pacing based at least in part on the conduction delays. After implant, a method may include measuring one or more conduction delays and optionally adjusting the electrode configuration (e.g., adapting a pacing therapy to a change in conduction delay(s)). Such electrode configuration selection or adjustment may consider electrode configurations for single site pacing and/or multi-site pacing.

Exemplary techniques presented herein may be used in conjunction with techniques that can optimize pacing parameters such as atrio-ventricular delay (e.g., with or without atrial pacing) and interventricular delay where a therapy uses bi-ventricular pacing. Such techniques may reduce frequency of ventricular or bi-ventricular pacing, enhance cardiac performance and/or increase longevity of an implanted cardiac pacing device. Further, such techniques may optimize pacing as a function of time or in response to changes in any of a variety of factors related to cardiac and/or device performance.

The following description begins with a discussion of exemplary implantable devices and associated components followed by a discussion of various exemplary methods that may be implemented using an implantable device and/or using an external device such as a programmer for an implantable device.

Exemplary Stimulation Device

The techniques described below are intended to be implemented in connection with any stimulation device that is configured or configurable to stimulate nerves and/or stimulate and/or shock a patient's heart.

Figure 1:
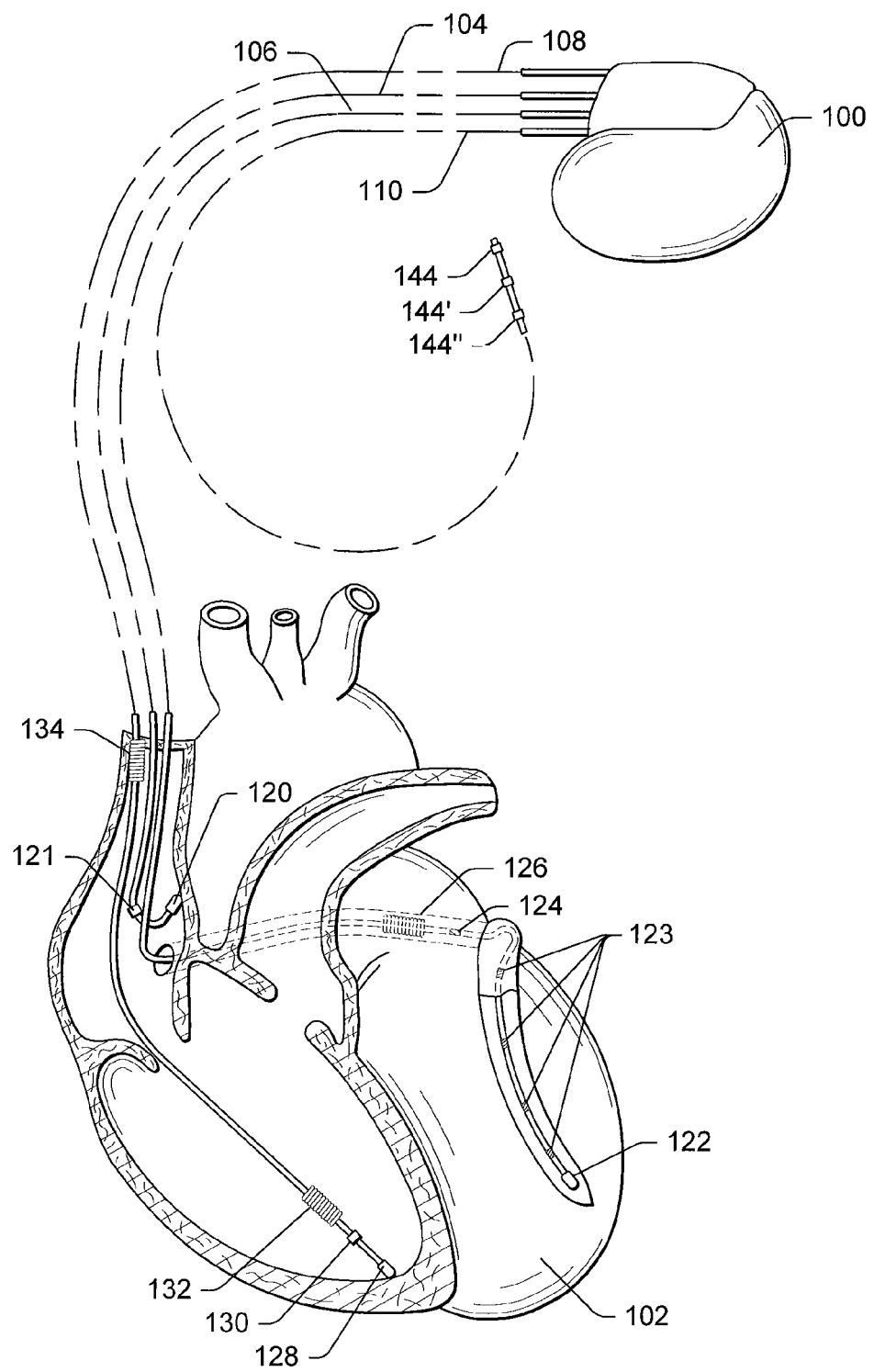
FIG. 1 is a simplified diagram illustrating an exemplary implantable stimulation device in electrical communication with at least three leads implanted into a patient's heart and at least one other lead for delivering stimulation and/or shock therapy. Other devices with fewer leads may also be suitable in some circumstances.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. Of course, such a lead may be positioned epicardially or at some other location to stimulate other tissue.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus (a venous structure) include, but may not be limited to, the great cardiac vein, the left marginal vein, the left posterior ventricular vein, the middle cardiac vein, and the small cardiac vein.

In the example of FIG. 1, the coronary sinus lead 106 includes a series of electrodes 123. In particular, a series of four electrodes are shown positioned in an anterior vein of the heart 102. Other coronary sinus leads may include a different number of electrodes than the lead 106. As described herein, an exemplary method may select one or more electrodes (e.g., from electrodes 123 of the lead 106) and determine characteristics associated with conduction in the heart to aid in ventricular pacing therapy.

An exemplary coronary sinus lead 106 may be used to receive ventricular cardiac signals (and optionally atrial signals) and/or to deliver left ventricular pacing therapy using, for example, at least one of the electrodes 123 and/or the tip electrode 122. The lead 106 optionally allows for left atrial pacing therapy, for example, using at least the left atrial ring electrode 124. The lead 106 optionally allows for shocking therapy, for example, using at least the left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference.

The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
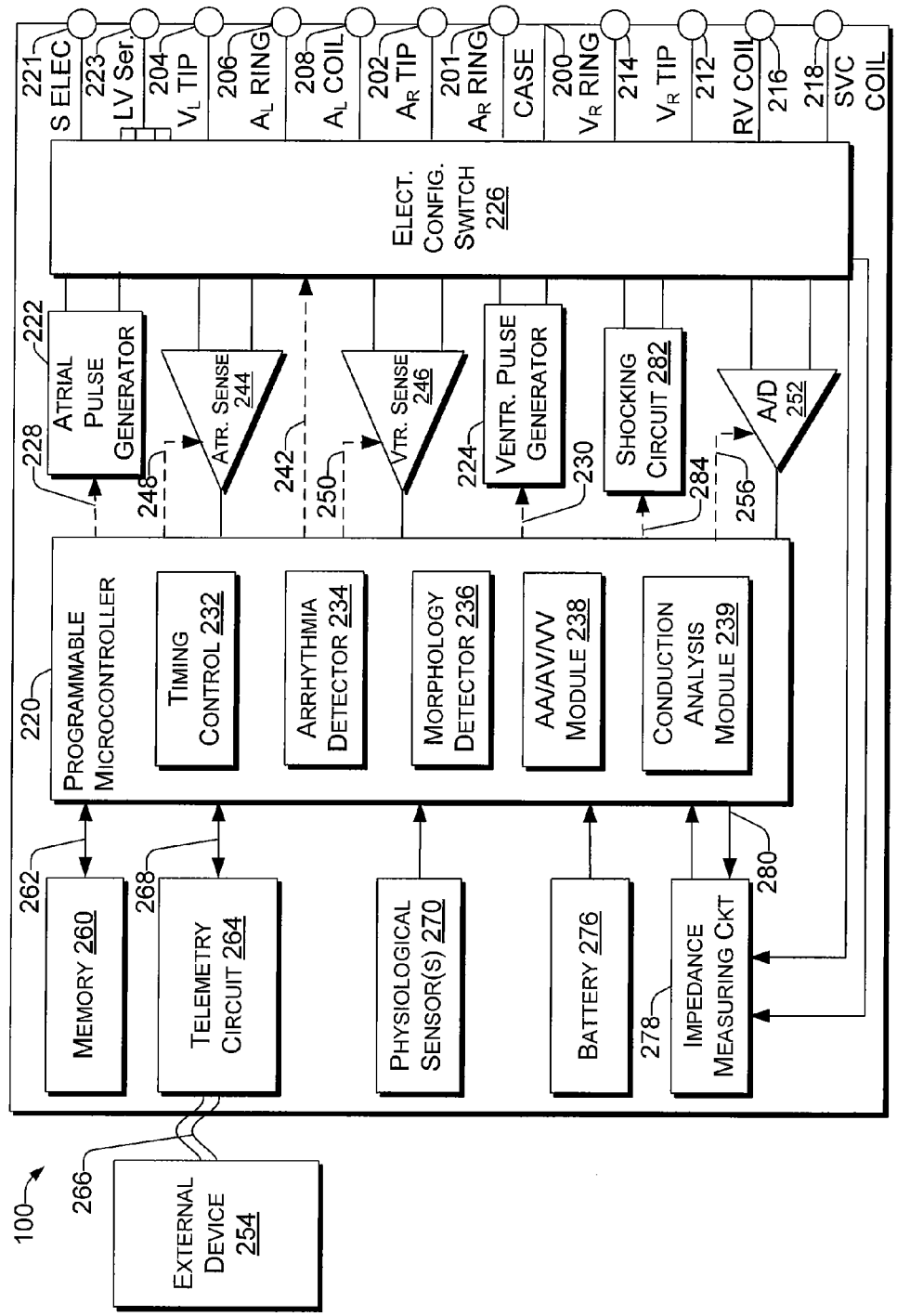
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes or electrode configurations. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

Other terminals may be included, for example, to accommodate other electrodes of other leads. Further, where appropriate, epicardial or other types of leads or electrodes may be connected to the device 100 or to a device in communication with the device 100 to provide for coordinated pacing therapy.

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

A terminal (LV Ser.) 223 allows for connection of a series of left ventricular electrodes. For example, the series of four electrodes 123 of the lead 106 may connect to the device 100 via the terminal 223. The terminal 223 and an electrode configuration switch 226 allow for selection of one or more of the series of electrodes and hence electrode configuration. In the example of FIG. 2, the terminal 223 includes four branches to the switch 226 where each branch corresponds to one of the four electrodes 123. An implantable device may include other terminals and/or terminal arrangements.

While the example of FIGS. 1 and 2 show a left ventricular lead with a series of electrodes, a right ventricular lead and/or other lead may include a series of electrodes. In such examples, appropriate terminals may be included along with circuitry for selecting one or more electrodes from a series of electrodes to thereby select a particular electrode configuration.

Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (e.g., AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an AA delay, AV delay and/or VV delay module 238 for performing a variety of tasks related to AA delay, AV delay and/or VV delay. This component can be utilized by the stimulation device 100 for determining desirable times to administer various therapies, including, but not limited to, ventricular stimulation therapy, biventricular stimulation therapy, resynchronization therapy, atrial stimulation therapy, etc. The AA/AV/VV module 238 may be implemented in hardware as part of the microcontroller 220, or as software/firmware instructions programmed into the device and executed on the microcontroller 220 during certain modes of operation. Of course, such a module may be limited to one or more of the particular functions of AA delay, AV delay and/or VV delay. Such a module may include other capabilities related to other functions that may be germane to the delays.

Microcontroller 220 further includes a conduction analysis module 239 for performing a variety of tasks related to measuring and/or analyzing measured conduction delays. Various conduction delays are discussed in more detail below and include interventricular conduction delays (IVCD). This component can be utilized by the stimulation device 100 for determining desirable electrode configurations, for example, using the switch and/or other features associated with a lead that includes a series of electrodes such as the lead 106. The module 239 may act in conjunction with one or more other modules such as the module 238 to determine times to administer various therapies. The conduction analysis module 239 may be implemented in hardware as part of the microcontroller 220, or as software/firmware instructions programmed into the device and executed on the microcontroller 220 during certain modes of operation. Such a module may include other capabilities related to other functions that may be germane to the conduction delays (e.g., monitoring cardiac condition, device condition, etc.).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include one or more physiologic sensors 270. A commonly used physiologic sensor is referred to as a "rate-responsive" sensor because it is typically used to adjust pacing stimulation rate according to the exercise state of the patient. The physiological sensors 270 may include a sensor capable of detecting changes in cardiac output. For example, with respect to pressure, U.S. Pat. No. 6,314,323, entitled "Heart stimulator determining cardiac output, by measuring the systolic pressure, for controlling the stimulation", to Ekwall, issued Nov. 6, 2001, discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output. The physiological sensors 270 may include one or more sensors that can detect changes in the physiological condition of the heart, diurnal changes in activity (e.g., detecting sleep and wake states), etc. The microcontroller 220 can be programmed or otherwise configured to respond to one or more sensor signals. Such a response may include adjusting one or more pacing parameters (such as rate, AA delay, AV delay, VV delay, etc.) and controlling the atrial and ventricular pulse generators, 222 and 224, which generate stimulation pulses.

While shown as being included within the stimulation device 100, it is to be understood that any of the one or more physiologic sensors 270 may be external to the stimulation device 100, yet still be implanted within or carried by the patient. Examples of physiologic sensors that may be implemented in the device 100 include known sensors that, for example, sense respiration (e.g., ventilation), pH of blood, ventricular gradient, cardiac output, preload, afterload, contractility, hemodynamics, blood gas (e.g., oxygen and/or carbon dioxide), pressure, and so forth. Another sensor that may be used is one that detects activity variance (e.g., where an activity sensor is monitored diurnally to detect a low variance in the measurement corresponding to a sleep state). For a complete description of an activity variance sensor see, for example, U.S. Pat. No. 5,476,483 (Bornzin et al.), issued Dec. 19, 1995, which is incorporated by reference herein.

The physiological sensors 270 may include one or more sensors for detecting patient movement and/or position. The physiological sensors 270 may include a minute ventilation (MV) sensor to sense minute ventilation, which is defined as the total volume of air that moves in and out of a patient's lungs in a minute. Signals generated by a position sensor and MV sensor can be passed to the microcontroller 220 for analysis in determining whether to adjust the pacing rate, etc. The microcontroller 220 may be configured to monitor one or more sensor signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode(s) may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As mentioned in the Background section, multi-site pacing can be beneficial. As described herein, a ventricular pacing therapy may use multi-site pacing to improve, for example, conduction velocity and uniformity of wave front propagation. Such improvements in ventricular wave front propagation can enhance hemodynamic performance. However, multi-site ventricular stimulation may not be needed all the time in all patients. Thus, various exemplary methods selectively and/or adaptively enable multi-site stimulation in patients in a manner that can reduce unnecessary deleterious effects of pacing, produce optimal/adequate cardiac resynchronization therapy (i.e., increase the responder rate), and prolong the device life by conserving battery power.

Figure 3:
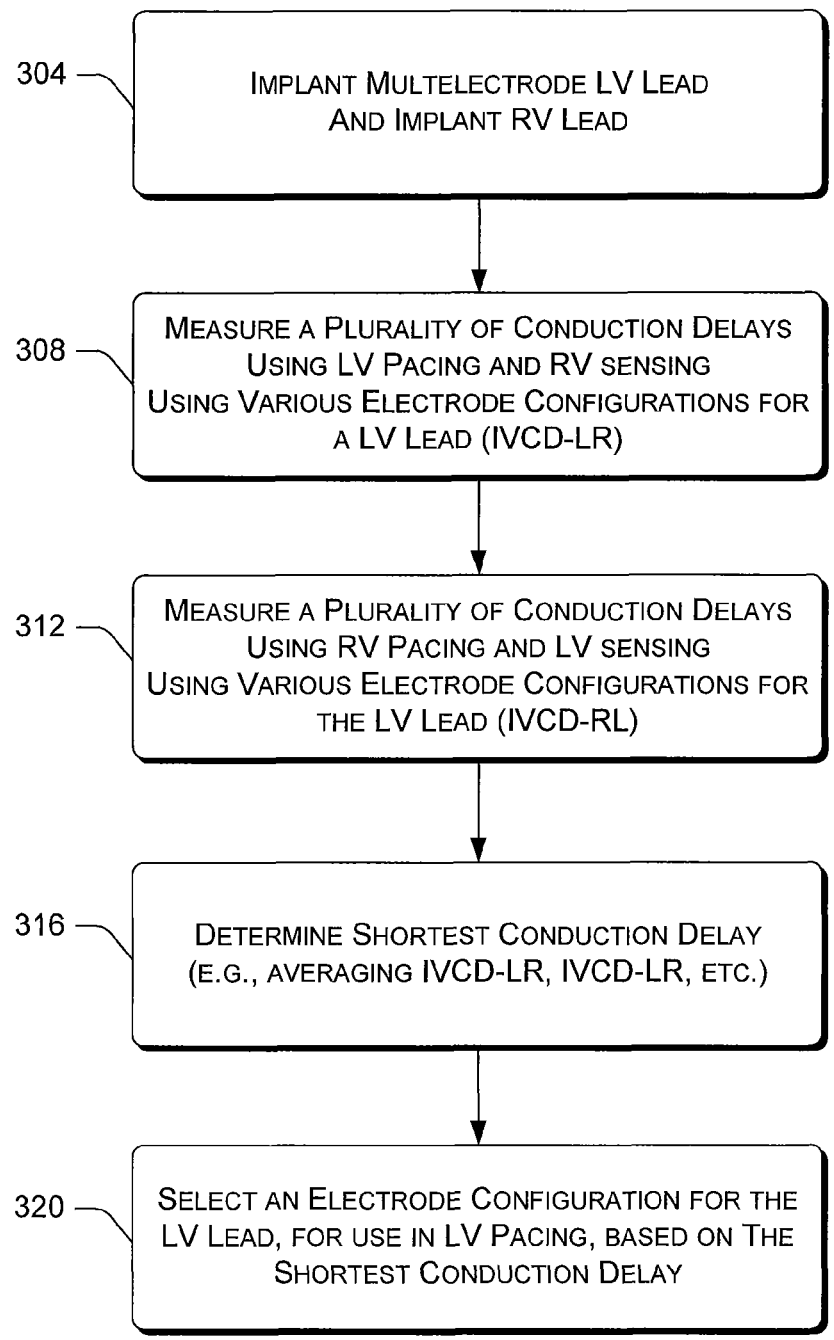
FIG. 3 is a block diagram of an exemplary method for selecting an electrode configuration for left ventricular pacing.

FIG. 3 shows an exemplary method 300 for selecting an electrode configuration for left ventricular pacing. The method 300 commences in an implantation block 304 that includes implanting a multielectrode LV lead (see, e.g., the lead 106 of FIG. 1) and implanting a RV lead (see, e.g., the lead 108 of FIG. 1). A measurement block 308 follows, which may occur during implantation. The measurement block 308 includes measuring an interventricular conduction delay for various electrode configurations for the LV lead. In this example, energy is delivered to the LV using the LV lead and cardiac activity associated with the delivered energy is sensed in the RV using the RV lead. The process is repeated for each of the LV lead electrode configurations to be tested. The interventricular conduction delay is referred to as IVCD-LR, as the wave front originates in LV and is sensed in the RV. For each LV lead electrode configuration, the delay may be determined as the time delay between delivery of energy in the LV and sensing the resultant wave front in the RV, as conducted through the heart (e.g., as conducted via the myocardium, blood, etc.). For the lead 106 of FIG. 1, the measurement block 308 may result in four single site IVCD-LR values: IVCD-$L_1$R, IVCD-$L_2$R, IVCD-$L_3$R and IVCD-$L_4$R. Where one or more multi-site electrode configuration is used, additional values may be produced.

Another measurement block 312, which may occur during implantation includes measuring another interventricular conduction delay. In this example, energy is delivered to the RV using the RV lead and cardiac activity associated with the delivered energy is sensed in the LV using the LV lead. The interventricular conduction delay is referred to as IVCD-RL, as the wave front originates in RV and is sensed in the LV. The delay may be determined as the time delay between delivery of energy in the RV and sensing the resultant wave front in the LV, as conducted through the heart (e.g., as conducted via the myocardium, blood, etc.). For the lead 106 of FIG. 1, the measurement block 312 may result in four single site IVCD-RL values: IVCD-$RL_1$, IVCD-$RL_2$, IVCD-$RL_3$ and IVCD-$RL_4$. Where one or more multi-site electrode configuration is used, additional values may be produced.

According to the method 300, a determination block 316 determines the shortest conduction delay. Such a determination may rely on statistical techniques such as averaging. For example, the IVCD-LR values may be averaged, the IVCD-RL values may be averaged and/or the IVCD-LR and IVCD-RL values added (for corresponding electrode configurations) and then averaged. Another parameter, referred to herein as $\Delta_{IVCD}$, is the difference between IVCD-LR and IVCD-RL for a given electrode configuration.

A selection block 320 selects an electrode configuration for the LV lead, for LV pacing, based at least in part on the shortest conduction delay. The selection block 320 may simply select the electrode configuration that produced the shortest conduction delay, as determined by block 316. As an alternative, the selection block 320 may use one or more other criteria to select an electrode configuration for LV pacing. For example, if the delivered energy for a particular LV lead electrode configuration caused activation of the phrenic nerve (diaphragm activation) or other tissue, then this electrode configuration may be excluded. In another example, if the LV lead electrode configuration is below a certain time, then this may indicate that the energy delivery and the sensing leads are too close to each other. If the leads are too close, the path of the current through the myocardium may be less than optimal.

According to FIG. 3, an exemplary method includes measuring a plurality of interventricular conduction delays using left ventricular pacing and right ventricular sensing where each interventricular conduction delay (IVCD-LR) corresponds to a different electrode configuration for a left ventricular lead, measuring a plurality of interventricular conduction delays using right ventricular pacing and left ventricular sensing where each interventricular conduction delay (IVCD-RL) corresponds to a different electrode configuration for the left ventricular lead, determining the shortest conduction delay and, based on the shortest conduction delay, selecting an electrode configuration for the left ventricular lead for use in left ventricular pacing. Such a method may be performed during implantation of a left ventricular lead and may include positioning the left ventricular lead based on the shortest conduction delay. As described herein, the electrode configurations for the left ventricular lead may include one or more single site electrode configurations and/or one or more multi-site electrode configurations. Various blocks or methods described herein are optionally implemented using one or more computer-readable media that include processor-executable instructions for performing a block or blocks of a method.

Figure 4:
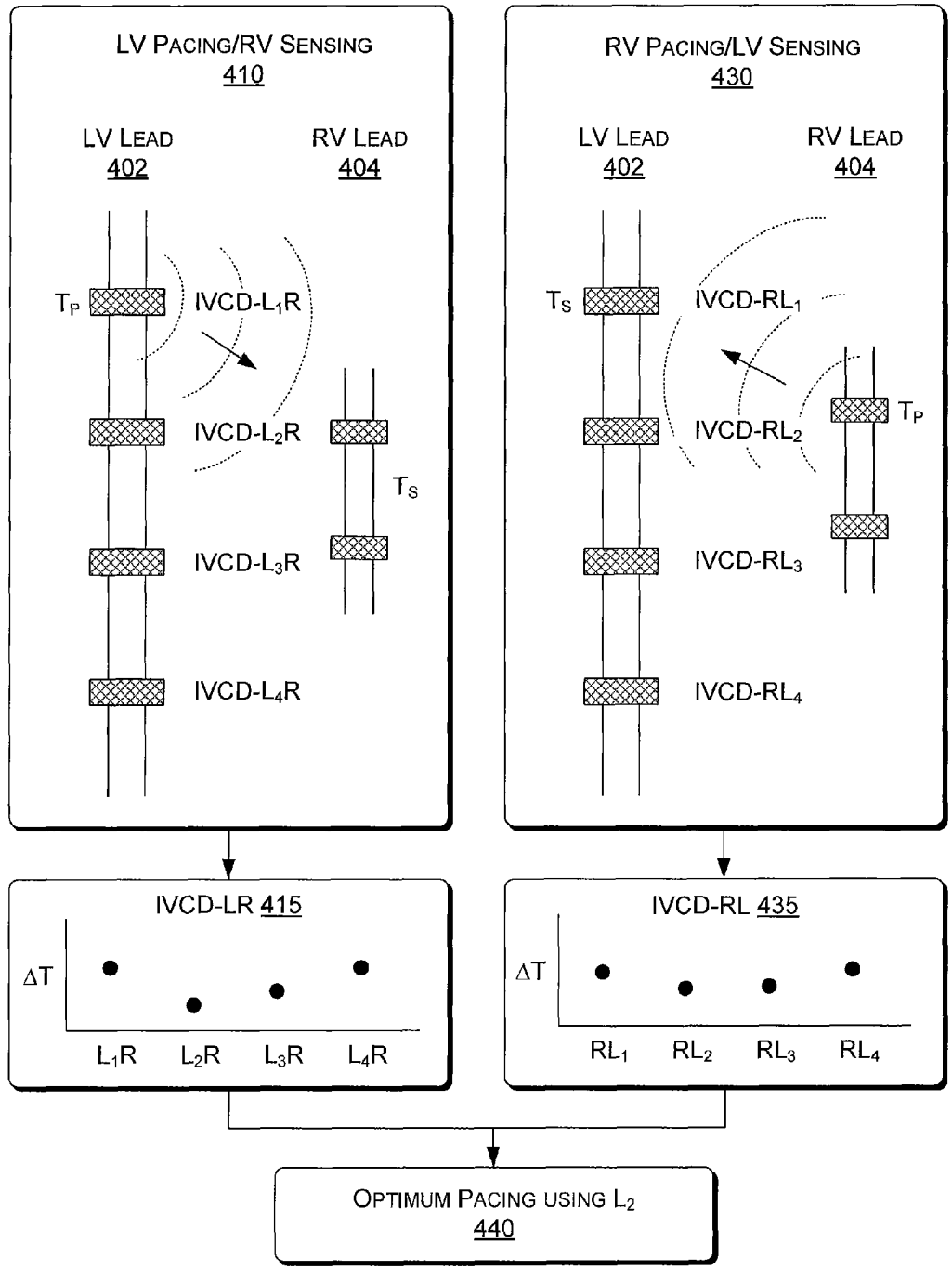
FIG. 4 is a diagram of a quadripolar left ventricular lead and a bipolar right ventricular lead and plots for interventricular conduction delays for use in selecting an optimum left ventricular lead electrode for left ventricular pacing.

FIG. 4 shows an exemplary method 400 that includes use of a quadripolar left ventricular lead 402 and a bipolar right ventricular lead 404. A LV pacing and RV sensing block 410 illustrates a wave front propagating from LV lead electrode $L_1$ (e.g., unipolar energy delivery) to the RV sensing electrodes (e.g., bipolar sensing); thus, corresponding to measurement of IVCD-L$_1$ R. An RV pacing and LV sensing block 430 illustrates a wave front propagating from the RV electrodes (e.g., bipolar energy delivery) to the LV lead electrode L$_1$ (e.g., unipolar sensing); thus, corresponding to measurement of IVCD-RL$_1$.

Plot 415 shows IVCD-LR as a time delay (ΔT) versus energy delivery/sensing configuration while plot 435 shows IVCD-RL as a time delay (ΔT) versus energy delivery/sensing configuration. The data of plots 415 and 435 may be used in a determination block 440 to determine optimum electrode configuration for LV pacing. In the example of FIG. 4, single site pacing using LV lead electrode L$_2$ corresponds to the shortest interventricular conduction delay.

Figure 5:
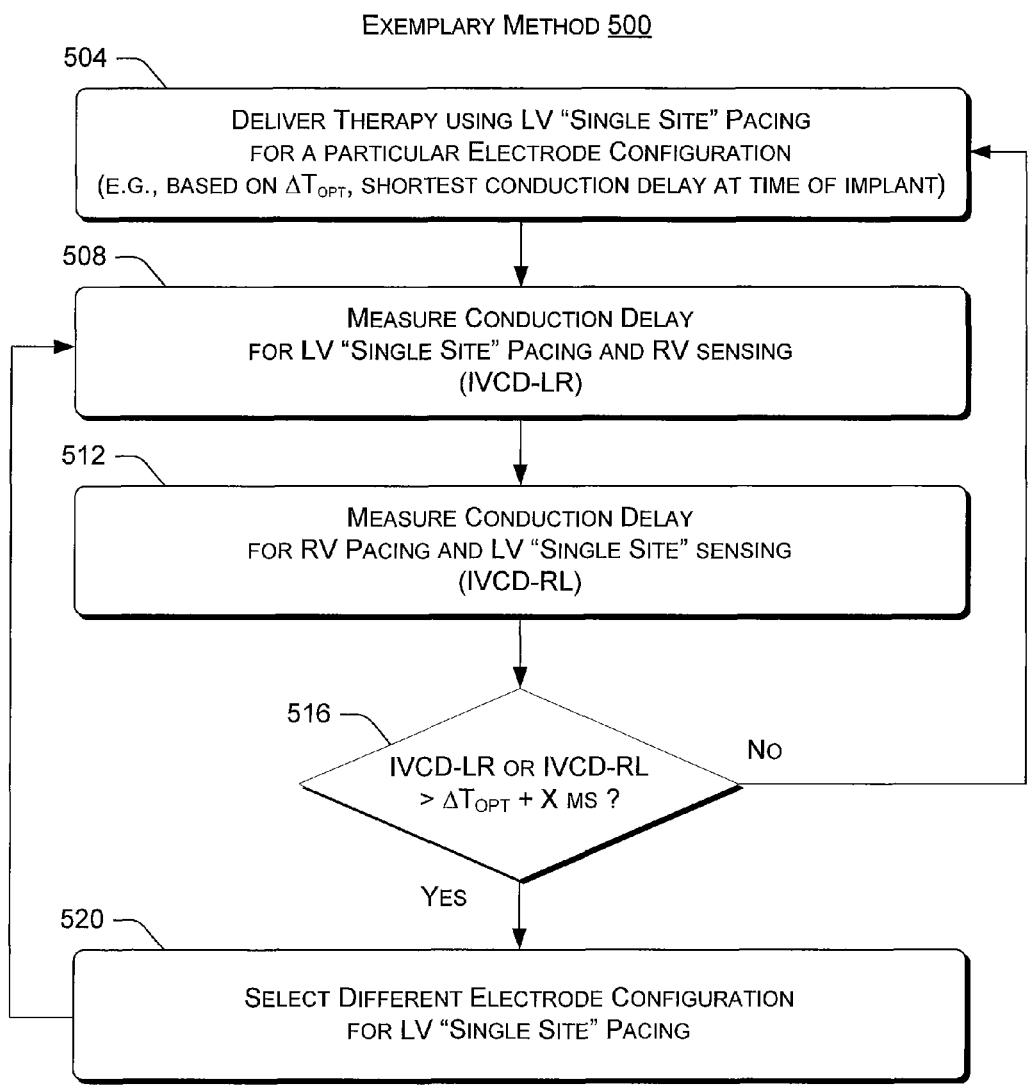
FIG. 5 is a block diagram of an exemplary method for monitoring interventricular conduction delays and optionally selecting a different left ventricular lead electrode for left ventricular pacing.

FIG. 5 shows an exemplary method 500 for monitoring interventricular conduction delays and optionally selecting a different LV lead electrode for LV pacing. The method 500 commences in a delivery block 504 that delivers a therapy using LV single site pacing for a particular electrode configuration, which may be based on an optimal delay (ΔT$_{Opt}$), determined at time of implant or at a time post-implant. The method 500 continues in a measurement block 508 that measures a conduction delay for the LV single-site pacing and RV sensing (IVCD-LR). Another measurement block 512 measures a conduction delay for RV pacing and LV single site sensing (IVCD-RL). A decision block 516 then decides if the IVCD-LR or IVCD-RL is greater than the optimal time (ΔT$_{Opt}$) plus a predetermined time (X ms). The predetermined time may be a time of approximately 20 ms, or other time as explained further below (see, e.g., FIG. 7).

If the decision block 516 decides that IVCD-LR or IVCD-RL is not equal to or greater than the specified criterion, then the method 500 continues at the delivery block 504. However, if the decision block 516 decides that IVCD-LR or IVCD-RL is equal to or greater than the specified criterion, then the method 500 continues at a selection block 520. The selection block 520 selects a different electrode configuration for LV single site pacing. The selection may be based on previously acquired conduction delay information such as information indicating an electrode configuration for the second shortest conduction delay or the selection may be based on a generic order or a predetermined order. Where such a selection occurs, the method 500 continues by measuring one or more conduction delays for the selected electrode configuration (e.g., per blocks 508 and/or 512). The same decision criterion may be applied to the measured conduction delay or delays and the selection repeated until the method arrives at an optimum electrode configuration (e.g., shortest conduction delay).

According to FIG. 5, an exemplary method includes delivering a cardiac pacing therapy using left ventricular, single site pacing, measuring an interventricular conduction delay using the left ventricular, single site pacing and right ventricular sensing (IVCD-LR), measuring an interventricular conduction delay using right ventricular pacing and the left ventricular, single site for sensing (IVCD-RL), comparing the interventricular conduction delays to an interventricular conduction delay limit and, based on the comparing, deciding whether to select a different site for left ventricular, single site pacing. Such a method may use an optimal interventricular conduction delay value as a limit and such a method may decide to select a different site for left ventricular, single site pacing if the interventricular conduction delays exceed the interventricular conduction delay limit. In the foregoing method, where a different site is selected, the method may include measuring one or more interventricular conduction delays using the different site.

In the foregoing method, left ventricular, single site pacing generally uses an electrode configuration that includes an electrode associated with a left ventricular lead where the left ventricular lead may include a series of electrodes (see, e.g., the lead 106, noting that a series may include more electrodes that the series 123). As already mentioned, left ventricular, single site pacing may use a case electrode of an implantable device (e.g., in a unipolar electrode configuration). As described herein, left ventricular, single site pacing may use an electrode configuration that includes two electrodes associated with a left ventricular lead (e.g., in a bipolar electrode configuration).

Figure 6:
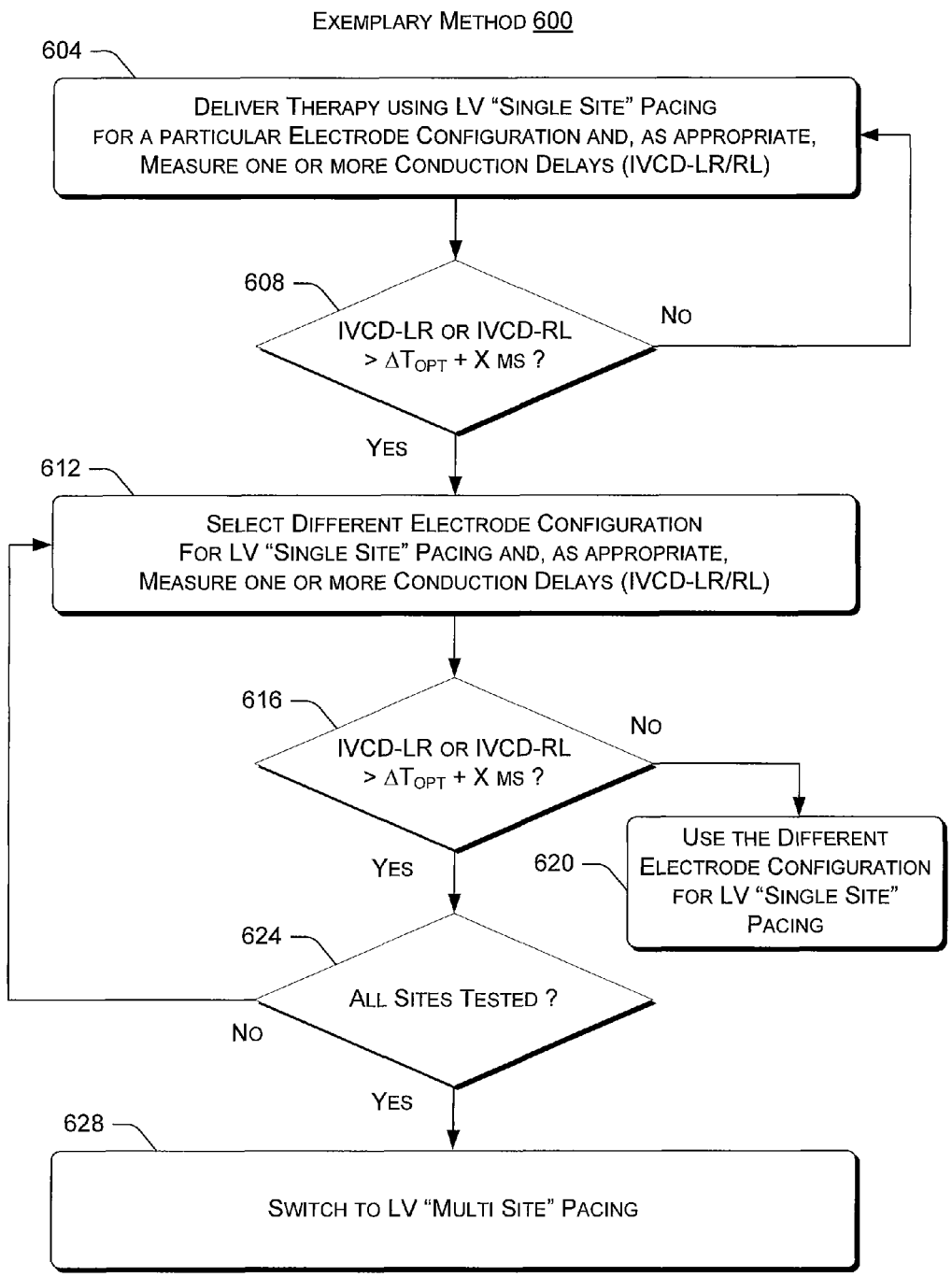
FIG. 6 is a block diagram of an exemplary method for optimizing left ventricular electrode configuration based at least in part on one or more interventricular conduction delays.

FIG. 6 shows an exemplary method 600 for optimizing LV electrode configuration based at least in part on one or more interventricular conduction delays. The method 600 commences in a delivery block 604 that delivers a therapy using LV single site pacing for a particular electrode configuration (e.g., based on an optimal delay (ΔT$_{Opt}$), determined at time of implant or at a time post-implant) and that measures, as appropriate, one or more conduction delays for the particular electrode configuration (e.g., IVCD-LR and/or IVCD-RL). A decision block 608 decides if the one or more measured conduction delays compare unfavorably to a decision criterion: ΔT$_{Opt}$+X ms. If the decision block 608 decides that the conduction delay or delays do not exceed the criterion, then the method 600 continues at the delivery and measurement block 604. However, if the conduction delay or delays exceed the criterion, then the method 600 continues at a selection and measurement block 612 that selects a different electrode configuration for LV single site pacing and that measures one or more conduction delays for the different electrode configuration.

As explained with respect to the decision block 608, a decision block 616 decides if the one or more conduction delays for the different electrode configuration exceed aforementioned criterion. If the decision block 616 decides that the criterion is not exceeded, then the method 600 continues in a use block 620 that uses the different electrode configuration for LV single site pacing. However, if the one or more conduction delays equal or exceed the criterion, then the method 600 continues in another decision block 624. The decision block 624 decides if all LV sites have been tested, for example, via the selection and measurement block 612. If the decision block 624 decides that all sites (e.g., electrode configurations) have not been tested, then the method 600 continues at the selection and measurement block 612. Otherwise, the method 600 continues at a switch block 628 that switches to LV multi-site pacing. The block 628 may select a particular electrode configuration for LV multi-site pacing and then decide if the selected electrode configuration is optimal. If the various electrode configurations for single site pacing and multi-site pacing fail to meet the criterion, then the method may issue an alert and select the best electrode configuration, whether associated with single site pacing or multi-site pacing.

Figure 7:
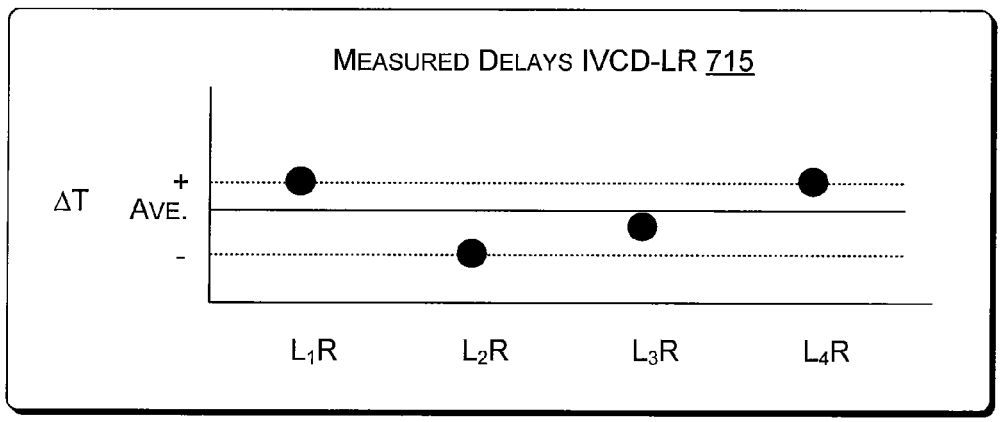
FIG. 7 is a series of exemplary plots and criteria for use in selecting or optimizing electrode configuration for ventricular pacing.
Figure 7:
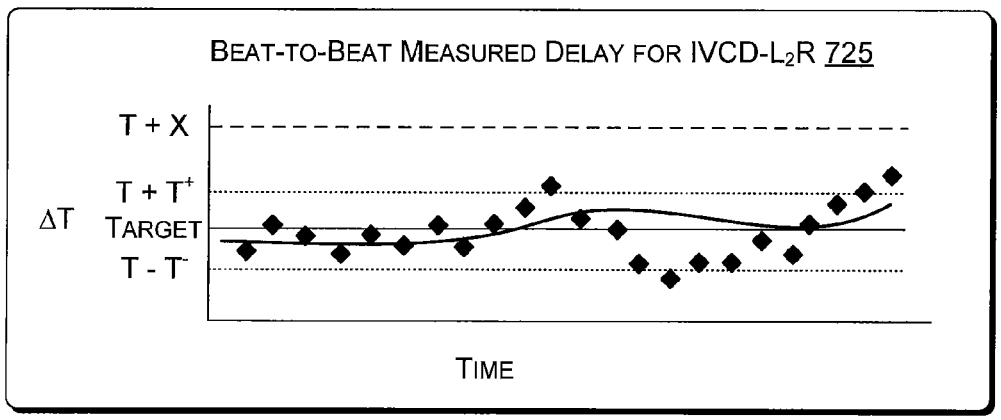

FIG. 7 shows an exemplary method 700 as associated with a series of plots 715, 725 and criteria 750 for use in selecting or optimizing electrode configuration for ventricular pacing. The methods 500 and 600 used a particular criterion, however, as explained with respect to the method 700 of FIG. 7, other criterion or criteria may be used. The plot 715 shows a series of measured conduction delays (IVCD-LR). From this data, an average, a minimum and a maximum may be determined, noting that any of a variety of statistical techniques may be used (e.g., mean, median, standard deviation, etc.). The data of the plot 715 may correspond to conduction delay values measured at implant or post-implant. The plot 725 shows beat-to-beat measured conduction delays (IVCD-L$_2$R) over time for about 24 cardiac cycles. In this example, a target value (T) is given along with positive and negative variances (T+T$^+$ and T−T$^−$). In addition, a value T+X appears as a value greater than the positive variance (T+T$^+$). A thick line represents a moving average of the conduction delay IVCD-L$_2$R, which may be averaged over a predetermined number of cardiac cycles and which may use weighting and/or a forgetting factor to reduce weight of one or more measured conduction delays based on acquisition time.

According to the method 700, the values X, T$^+$ and/or T$^−$ may be determined at least in part on the basis of conduction delay information acquired at implant, or optionally at another time. The criteria block 750 includes various beat-to-beat criteria and moving average criteria that may be used in adjusting or optimizing ventricular pacing, for example, as explained with respect to the decision blocks of the method 500 and the method 600.

Figure 8:
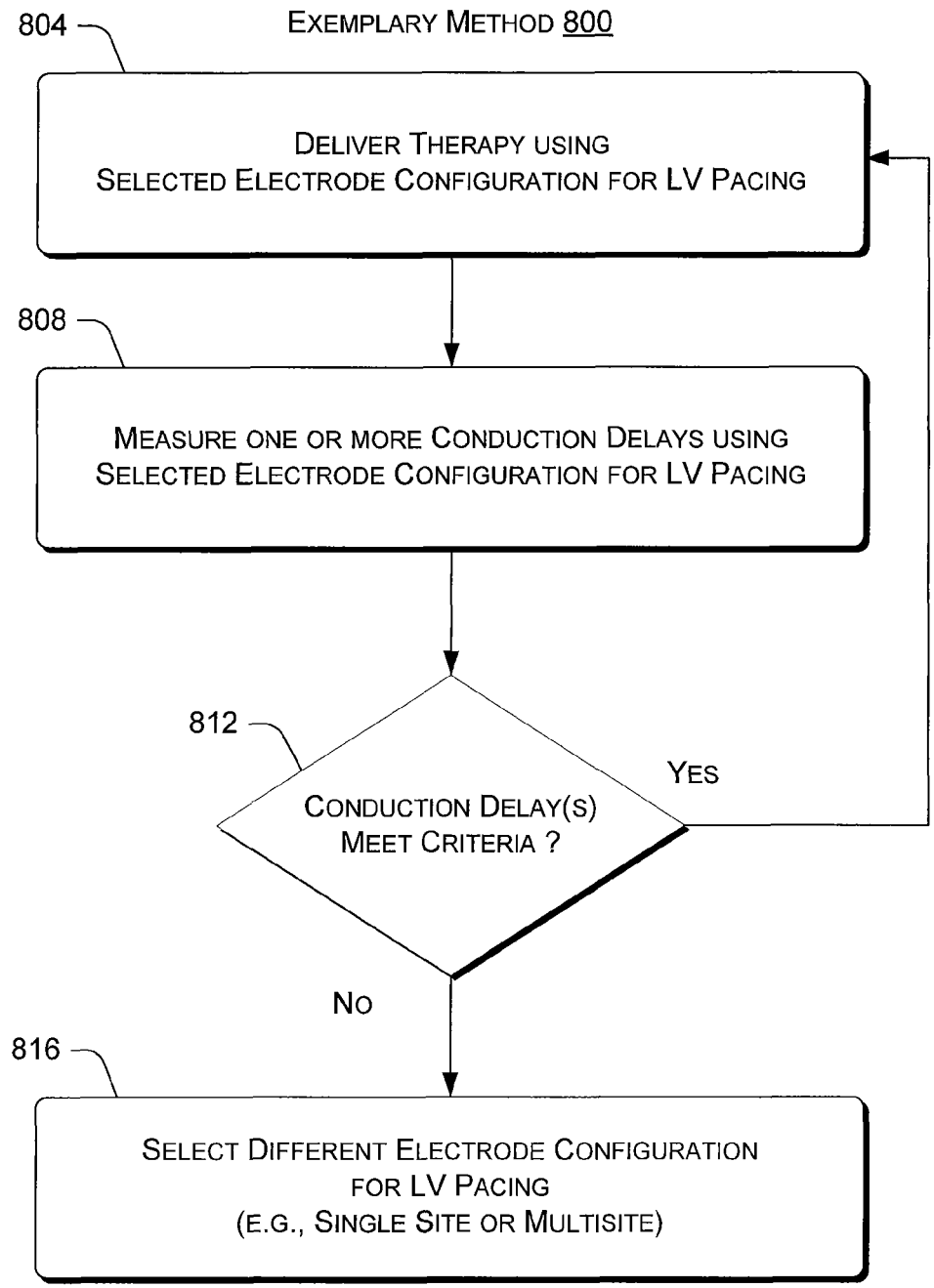
FIG. 8 is a block diagram of an exemplary method for selecting or optimizing electrode configuration for ventricular pacing based on comparing one or more interventricular conduction delays to one or more criteria.

FIG. 8 shows an exemplary method 800 for selecting or optimizing electrode configuration for ventricular pacing based on comparing one or more interventricular conduction delays to one or more criteria. The one or more criteria may be based, at least in part, on previously acquired conduction delay values or the one or more criteria may be based on a model or general knowledge of cardiac mechanics for a patient or a group of patients.

The method 800 commences in a delivery block 804 that delivers a therapy using a selected electrode configuration for LV pacing. A measurement block 808 measures one or more conduction delays using the selected electrode configuration for LV pacing. A decision block 812 follows that decides if the one or more conduction delays meet the criteria, where meeting the criteria indicates that the selected electrode configuration is suitable for delivery of the therapy. If the decision block 812 decides that the one or more conduction delays meet the criteria, then the method 800 continues at the delivery block 804. However, if the decision block 812 decides that the one or more conduction delays do not meet the criteria, then the method 800 continues at a selection block 816 that selects a different electrode configuration for LV pacing, which may be associated with delivery of therapy using single site pacing or multi-site pacing.

Figure 9:
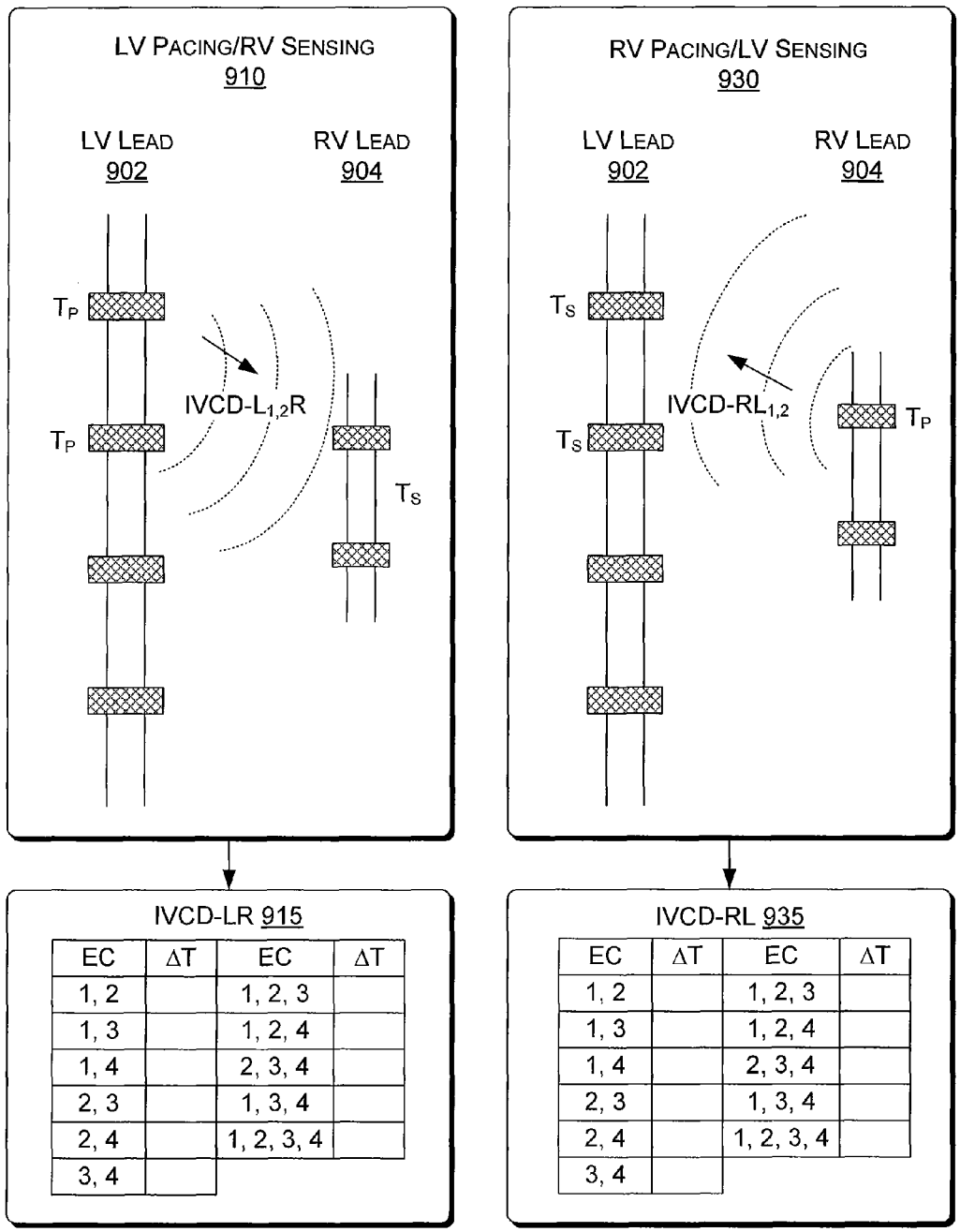
FIG. 9 is a diagram of a quadripolar left ventricular lead and a bipolar right ventricular lead and plots for interventricular conduction delays for use in selecting an optimum left ventricular lead multiple electrode configuration for left ventricular pacing.

FIG. 9 shows an exemplary method 900 that includes use of a quadripolar left ventricular lead 902 and a bipolar right ventricular lead 904. A LV pacing and RV sensing block 910 illustrates a wave front propagating from LV lead electrodes L$_1$ and L$_2$ (e.g., unipolar or multi-polar energy delivery) to the RV sensing electrodes (e.g., bipolar sensing); thus, corresponding to measurement of IVCD-L$_{1,2}$R. An RV pacing and LV sensing block 930 illustrates a wave front propagating from the RV electrodes (e.g., bipolar energy delivery) to the LV lead electrodes L$_1$ and L$_2$ (e.g., unipolar or multi-polar sensing); thus, corresponding to measurement of IVCD-RL$_{1,2}$. With respect to unipolar energy delivery or unipolar sensing using the electrodes L$_1$ and L$_2$, these electrodes may be both anodes or both cathodes where another electrode such as a case electrode (e.g., the case 200 of FIG. 2) is used as a cathode or an anode, respectively. With respect to multi-polar energy delivery or sensing, one of the electrodes L$_1$ or L$_2$ may be a cathode or an anode while the other is an anode or a cathode, respectively.

Data table 915 shows various electrode configurations (EC) for the LV lead 902 and IVCD-LR times as time delays ($\Delta$T) while the data table 935 shows various electrode configurations (EC) for the LV lead 902 and IVCD-RL times as time delays ($\Delta$T). The data tables 915 and 935 may be used to determine an optimum electrode configuration for LV pacing or for other purposes, for example, as described with respect to FIG. 12.

Figure 10:
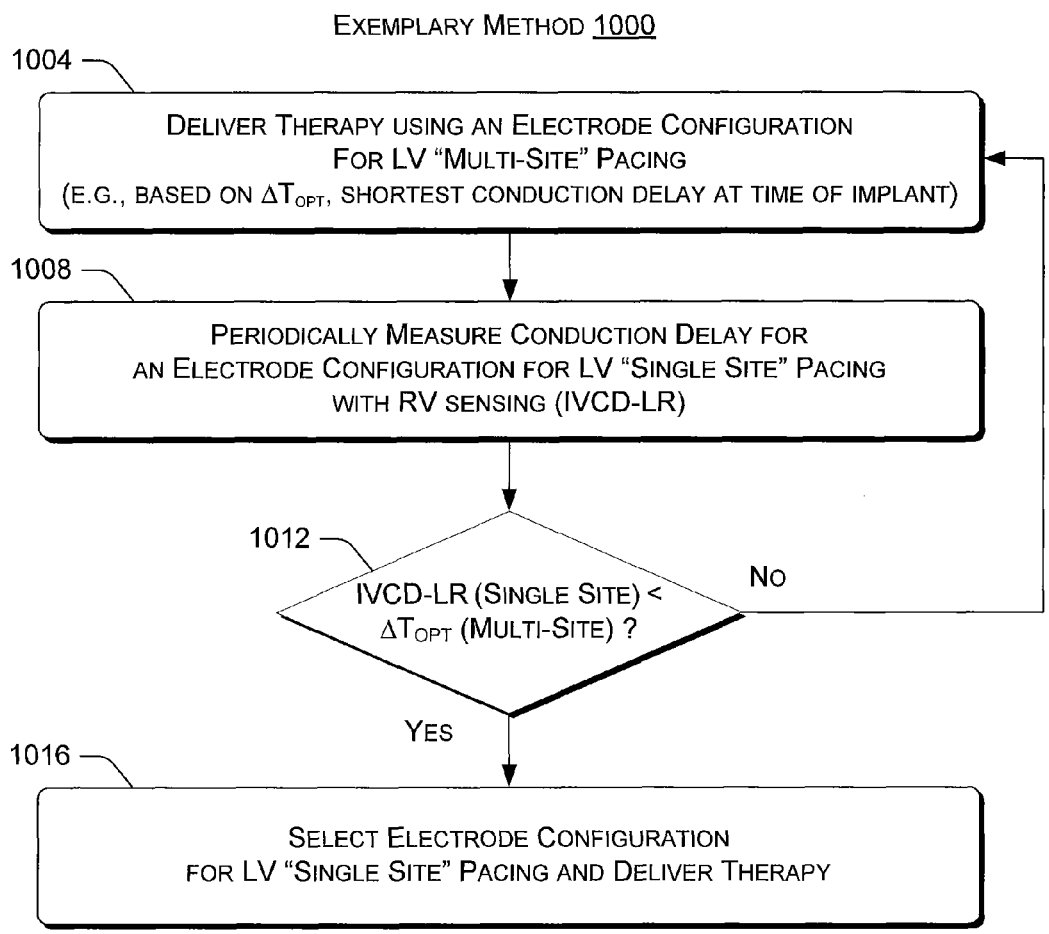
FIG. 10 is a block diagram of an exemplary method for periodically measuring interventricular conduction delays for selecting or optimizing left ventricular pacing.

FIG. 10 shows an exemplary method 1000 for periodically measuring interventricular conduction delays for selecting or optimizing LV pacing. The method 1000 commences in a delivery block 1004 that delivers a therapy using an electrode configuration for LV multi-site pacing. The particular electrode configuration may be based on an optimal $\Delta T_{Opt}$, for example, determined at implant or post-implant.

A measurement block 1008 periodically measures a conduction delay for an electrode configuration for LV single site pacing. For example, the method 1000 may operate according to a schedule where once a day, measurement occurs for one or more electrode configurations for LV single site pacing. Such measurement may occur based on a number of cardiac cycles, in response to a change in a pacing parameter, a change in a cardiac condition, a command issued by a programmer for an implantable device, a command delivered by an external device (e.g., telephone), etc.

In the example of FIG. 10, the conduction delay is an interventricular conduction delay for LV pacing and RV sensing (IVCD-LR). A decision block 1012 then decides if the IVCD-LR value is less than an optimal value ($\Delta T_{Opt}$) or a target value (e.g., T) associated with the electrode configuration for multi-site pacing. If the decision block 1012 decides that the IVCD-LR value is not less than the criterion, then the method 1000 continues at the delivery block 1004. However, if the decision block 1012 decides that the IVCD-LR value is less than the criterion, then the method 1000 continues in a selection and delivery block 1016 that selects the electrode configuration for LV single site pacing and delivers therapy using LV single site pacing. Thus, the method 1000 aims to periodically check whether single site pacing may be used instead of multi-site pacing. As already mentioned, multi-site pacing may require more energy and hence may deplete an implanted device's energy store more rapidly than single site pacing. Of course, cardiac performance, quality of life concerns, scheduled replacement for an implanted device or device power source may be taken into consideration when implementing the method 1000 or when otherwise deciding whether to delivery single site or multi-site ventricular pacing.

An exemplary method that delivers multi-site ventricular pacing may switch to single site ventricular pacing to increase longevity of an implanted device. For example, if a battery level falls below a particular limit or if a battery's drain rate exceeds a certain limit, then an exemplary method may inhibit delivery multi-site pacing or lock the therapy into a single site pacing mode.

Figure 11:
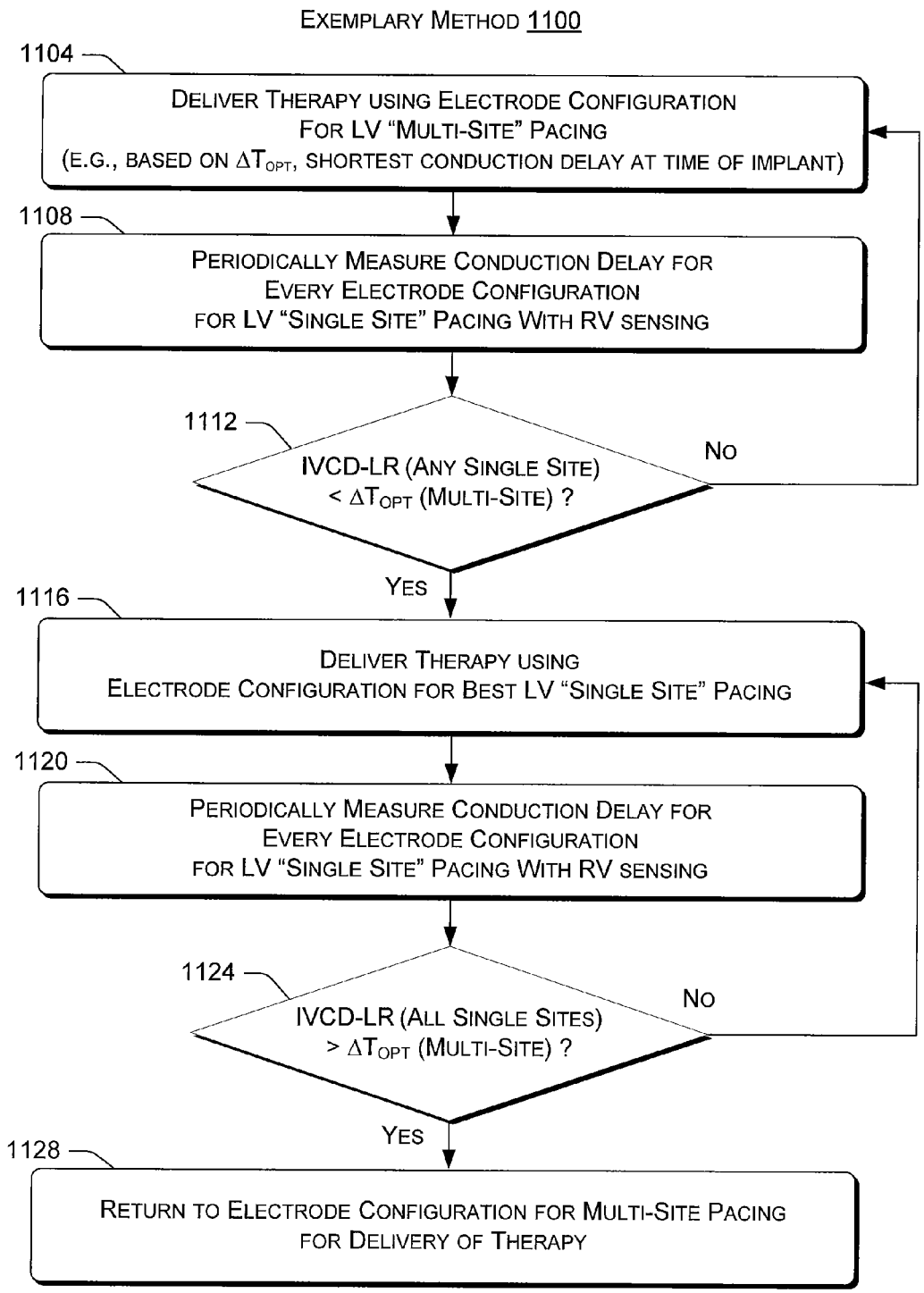
FIG. 11 is a block diagram of an exemplary method for periodically measuring interventricular conduction delays for deciding whether to use "single site" left ventricular pacing or to use "multi-site" left ventricular pacing.

FIG. 11 shows an exemplary method 1100 for periodically measuring interventricular conduction delays for deciding whether to use "single site" LV pacing or to use "multi-site" LV pacing. The method 1100 commences in a delivery block 1104 that delivers therapy using an electrode configuration for LV multi-site pacing. A measurement block 1108 occurs periodically to measure conduction delay(s) for every electrode configuration for LV single site pacing with RV sensing (IVCD-LR).

A decision block 1112 compares each conduction delay(s) to a criterion associated with multi-site pacing. For example, the criterion may be a conduction delay value that was used to select the electrode configuration for multi-site pacing. Such a conduction delay value may be a value determined at implant or post-implant. If the decision block 1112 decides that none of the IVCD-LR values are less than the criterion, then the method 1100 continues at the delivery block 1104.

However, if the decision block 1112 decides that one or more of the IVCD-LR values are equal to or less than the criterion, then the method 1100 continues at a delivery block 1116 that delivers therapy using the electrode configuration for the best performing LV single site pacing (e.g., the shortest IVCD-LR).

If the method 1100 switches to single site pacing, then a measurement block 1120 periodically measures conduction delay for every electrode configuration for LV single site pacing with RV sensing, as explained with respect to the measurement block 1108. However, the decision block 1124 that follows differs from the decision block 1112 in that it seeks to decide whether a switch back to multi-site pacing should occur. More specifically, if the decision block 1124 decides that IVCD-LR values for all single sites are less than or equal to the criterion (e.g., same criterion as for the decision block 1112), then the method 1100 continues with single site pacing. However, if the decision block 1124 decides that IVCD-LR values for all single site are greater than the criterion, then the method 1100 enters block 1128 that returns to an electrode configuration for multi-site pacing for delivery of the therapy.

Figure 12:
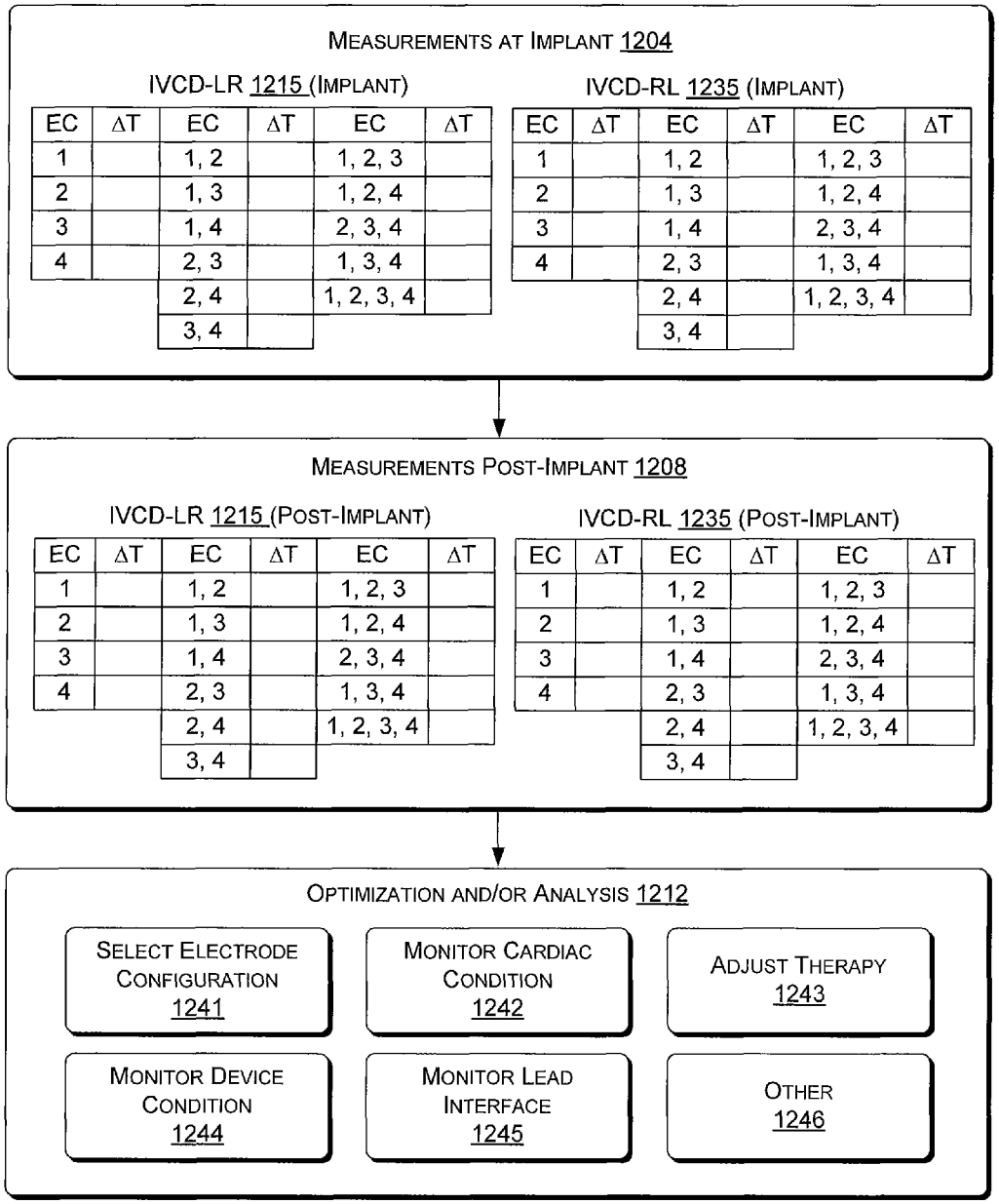
FIG. 12 is a block diagram of an exemplary method that includes measuring interventricular conduction delays at the time of implant of a ventricular pacing lead, measuring interventricular conduction delays post-implant and optimizing therapy and/or performing an analysis using the measured interventricular conduction delays.

FIG. 12 shows an exemplary method 1200 that includes measuring interventricular conduction delays at the time of implant of a ventricular pacing lead 1204, measuring interventricular conduction delays post-implant 1208 and optimizing therapy and/or performing an analysis using the measured interventricular conduction delays 1212.

The measurement at implant block 1204 shows a table for IVCD-LR 1215 and a table for IVCD-RL 1235. Various electrode configurations are indicated that correspond to the quadripolar lead 106 of FIG. 1. Other leads may be used that include fewer or more electrodes and the tables 1215 and 1235 may be altered accordingly. At implant the data tables 1215 may be used to position a lead or leads with respect to the heart. For example, a LV lead may be repositioned if none of the values in the table 1215 or the table 1235 meet a specified criterion or criteria. Alternatively, a LV lead may be positioned at three different locations in the heart (e.g., deep, medium and shallow) and information acquired for each of the three locations. An analysis of the information (e.g., conduction delay information as in tables 1215 and/or 1235) may be used to select one of the locations or to select a different location (e.g., deeper, intermediate deep/medium, intermediate medium/shallow, or shallower). As already mentioned, criteria may pertain to conduction delay information or other information (e.g., other tissue or nerve stimulation or risk of stimulation, etc.).

The measurement post-implant block 1208 shows the same table for IVCD-LR 1215 and the same table for IVCD-RL 1235, however, these would include values that correspond to a post-implant scenario, where the lead or leads are generally fixed. While only one set of post-implant tables are shown in FIG. 12, an exemplary method may use data acquired at various times after implant. For example, such tables may be generated once a day, once a week, once a month, etc.

The optimization and/or analysis block 1212 shows various actions that may be based at least in part on the information acquired at implant 1204 and the information acquired post-implant 1208. Actions include selection of electrode configuration 1241, monitoring cardiac condition 1242, adjusting therapy 1243, monitoring device condition 1244, monitoring lead/tissue interface 1245, and other 1246.

As discussed with respect to the implantable device 100 of FIGS. 1 and 2, one or more physiological sensors 270 may be used to sense any of a variety of information. The optimization and/or analysis block 1212 of FIG. 12 may use information sensed by one or more physiologic sensors. For example, a pressure sensor may sense blood pressure during delivery of a pacing therapy where the pacing therapy uses a particular electrode configuration. The blood pressure information may be used in conjunction with the measurements 1204 and/or the measurements 1208 to optimize and/or analyze cardiac performance. In general, sensed information may be used with any of the action blocks 1241-1246, as desired. As described with respect to FIG. 14, below, control logic (e.g., for an implantable device) may use sensed information to adjust or optimize an electrode configuration.

Figure 13:
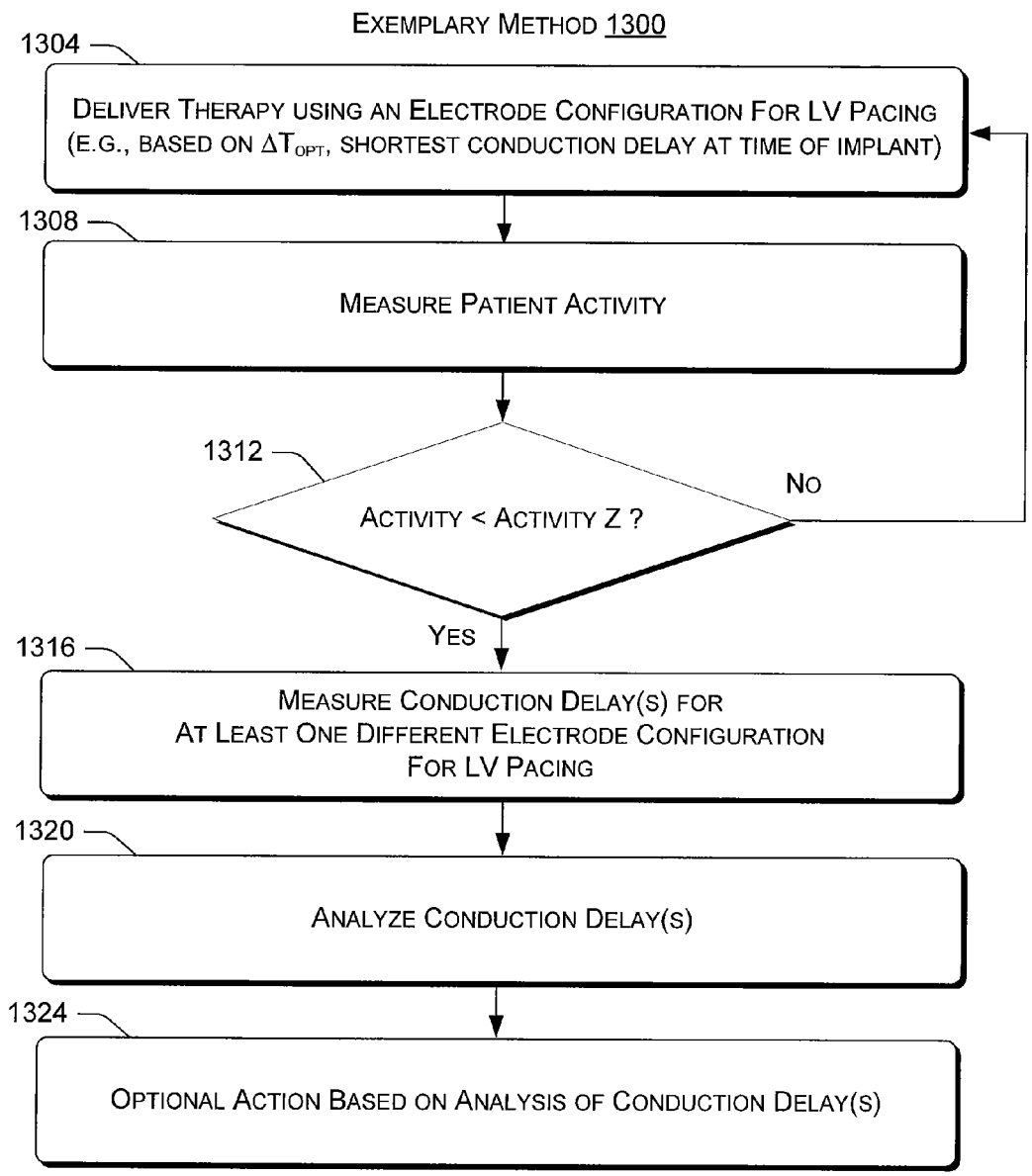
FIG. 13 is a block diagram of an exemplary method that includes measuring patient activity, deciding if patient activity meets one or more criteria and then measuring one or more interventricular conduction delays.

FIG. 13 shows an exemplary method 1300 that includes delivery a therapy 1304, measuring patient activity 1308, deciding if patient activity meets one or more criteria 1312 and then measuring one or more interventricular conduction delays 1316, analyzing the delay(s) 1320 and optionally performing an action based at least in part on such an analysis 1324. The delivery block 1304 delivers a therapy using an electrode configuration for LV pacing, which may be for single site pacing or multi-site pacing. A measurement block 1308 measures patient activity. For example, as discussed with respect to the device 100 of FIGS. 1 and 2, an implantable device may include one or more physiological sensors 270 (e.g., accelerometer, position sensor, etc.) suited to measure or otherwise detect a level of patient activity.

According to the method 1300, a decision block 1312 decides if the patient's activity is less than a predetermined activity level, which may be an activity level associated with rest or sleep. If the decision block 1312 decides that the activity is greater than the predetermined level, then the method continues at the delivery block 1304. However, if the activity level is less than or equal to the predetermined activity level, the method 1300 continues in a measurement block 1316 that measures a conduction delay(s) for at least one different electrode configuration for LV pacing. An analysis block 1320 follows that analyzes the conduction delay(s), for example, to determine whether the electrode configuration of the delivery block 1304 should be used or whether a change to the electrode configuration for LV pacing should occur. The analysis block 1320 may perform other one or more other analyses, for example, the analysis block 1320 may compare the measured conduction delay(s) to one or more criterion germane to cardiac performance. Such an analysis may be used to assess cardiac condition, response to therapy, etc. (see, e.g., block 1212 of FIG. 12). As indicated by the optional action block 1324, the method 1300 may perform an action based at least in part on an analysis. For example, the block 1324 may call for a change in electrode configuration, issuance of an alert, a change in one or more pacing parameters, etc.

Figure 14:
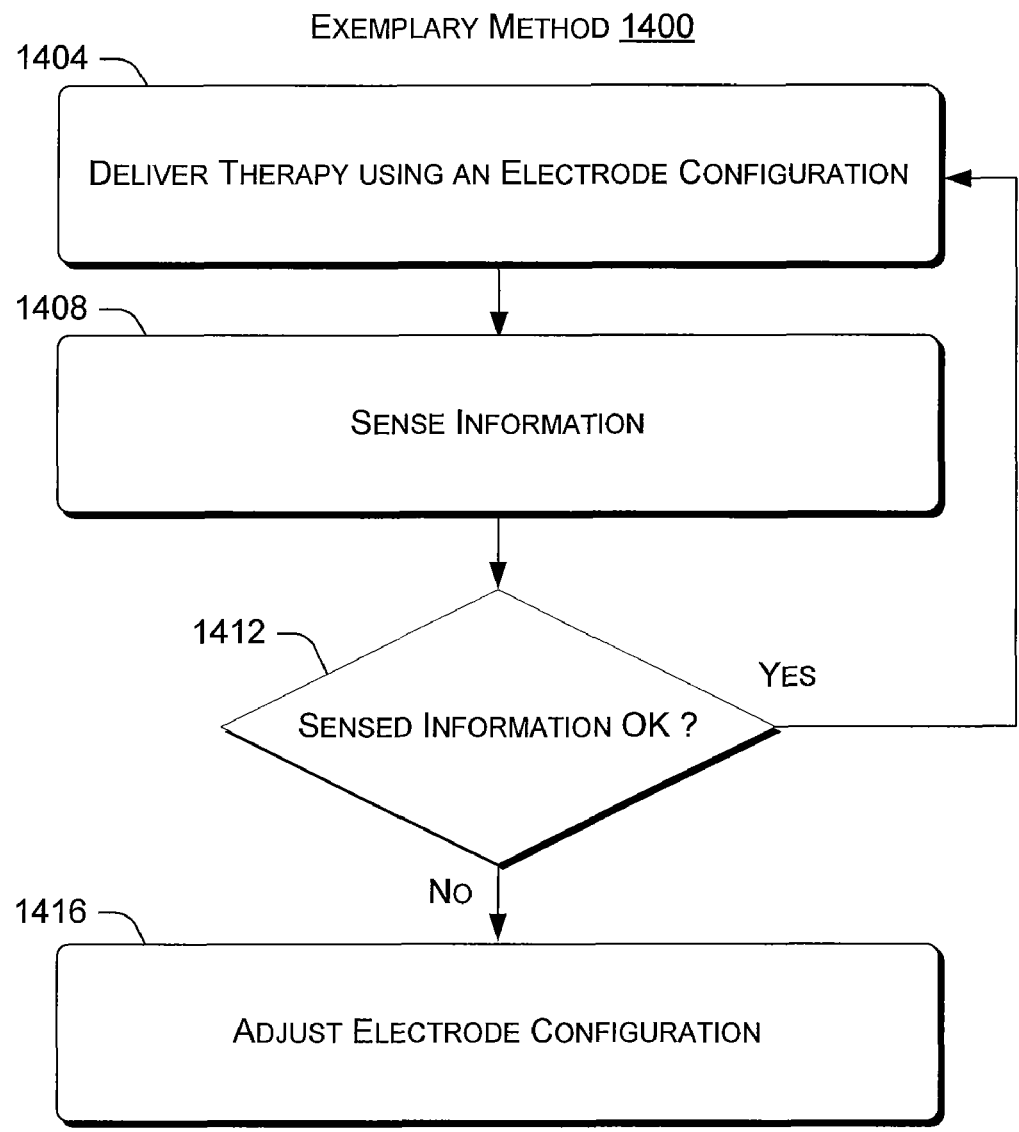
FIG. 14 is a block diagram of an exemplary method that includes sensing information and then deciding whether to change an electrode configuration based on the sensed information.

FIG. 14 shows an exemplary method 1400 that uses sensed information to optimize or adjust electrode configuration. The method 1400 commences in a delivery block 1404 where an implantable device delivers stimulation energy to the heart using a selected electrode configuration. A sense block 1408 senses information using one or more physiological sensors (see, e.g., the one or more sensors 270 of the device 100 of FIGS. 1 and 2). According to the method 1400, sensing may occur before, during and/or after delivery of stimulation energy to the heart. Further, a sensor may be external to a patient's body yet configured to communicate sensed information to an implantable device.

In general, an implantable device includes control logic that receives information and controls delivery of energy to the heart based at least in part on the received information. For example, sense block 1408 may sense pressure information. In turn, control logic may compare the sensed pressure information to one or more criteria such as a pressure limit and then decide whether to call for a particular control action. In the example of FIG. 14, a decision block 1412 decides if the sensed information is OK (e.g., with respect to one or more criteria). If the decision block 1412 decides that the sensed information is not OK, then an adjustment block 1416 adjusts the electrode configuration; whereas, if the decision block 1412 decides that the sensed information is OK, then the method 1400 continues at the delivery block 1404 where the implantable device continues to use the selected electrode configuration to delivery stimulation energy to the heart.

In the example of FIG. 14, the method 1400 optionally measures one or more conduction delays (e.g., IVCD-RL, IVCD-LR) and optionally uses such measurements to adjust an electrode configuration or take other action. For example, sensed information germane to patient condition (patient activity, heart rate, patient position, edema, etc.) may be used to classify or analyze a conduction delay.

Figure 15:
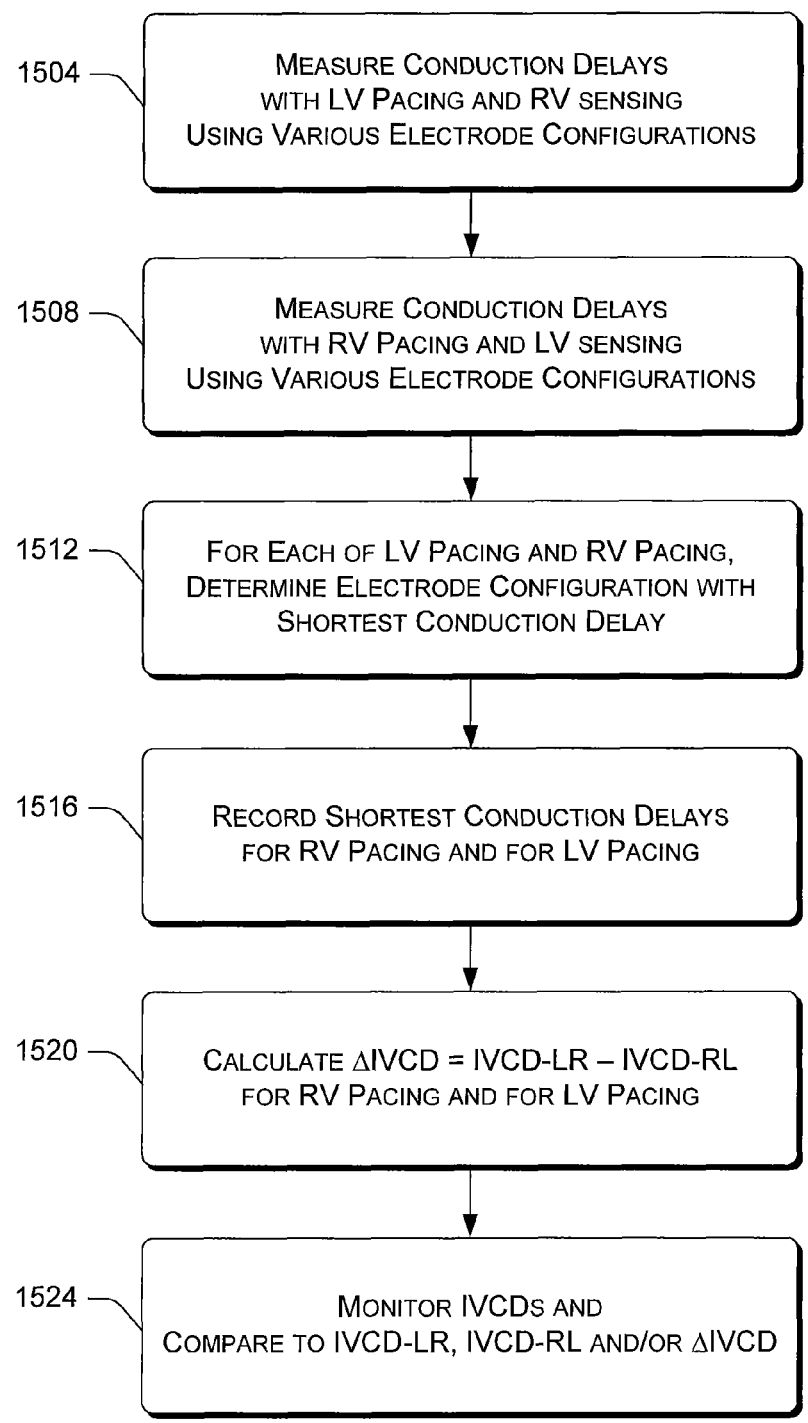
FIG. 15 is a block diagram of an exemplary method that includes monitoring one or more interventricular conduction delays.

FIG. 15 shows an exemplary method 1500 that includes monitoring one or more interventricular conduction delays. The method 1500 commences in a measurement block 1504 that measures conduction delays with LV pacing and RV sensing using various electrode configurations and a measurement block 1508 that measures conduction delays with RV pacing and LV sensing using various electrode configurations. A determination block 1512 then determines, for each of LV pacing and RV pacing, the electrode configuration with the shortest conduction delay. A recordation block 1516 records at least the shortest conduction delays, which may be used for any of a variety of purposes.

As already mentioned, a parameter $\Delta_{IVCD}$ exists and a calculation block 1520 calculates this parameter for both RV pacing and LV pacing. A monitoring block 1524 monitors the IVCDs (e.g., periodically or other basis) and then compares these values with the recorded IVCD-LR, IVCD-RL and/or $\Delta$IVCD values for RV pacing and/or LV pacing. In general, the method 1500 is particularly suited for use with therapies that deliver bi-ventricular pacing therapy (e.g., bi-ventricular cardiac resynchronization therapy).

Figure 16:
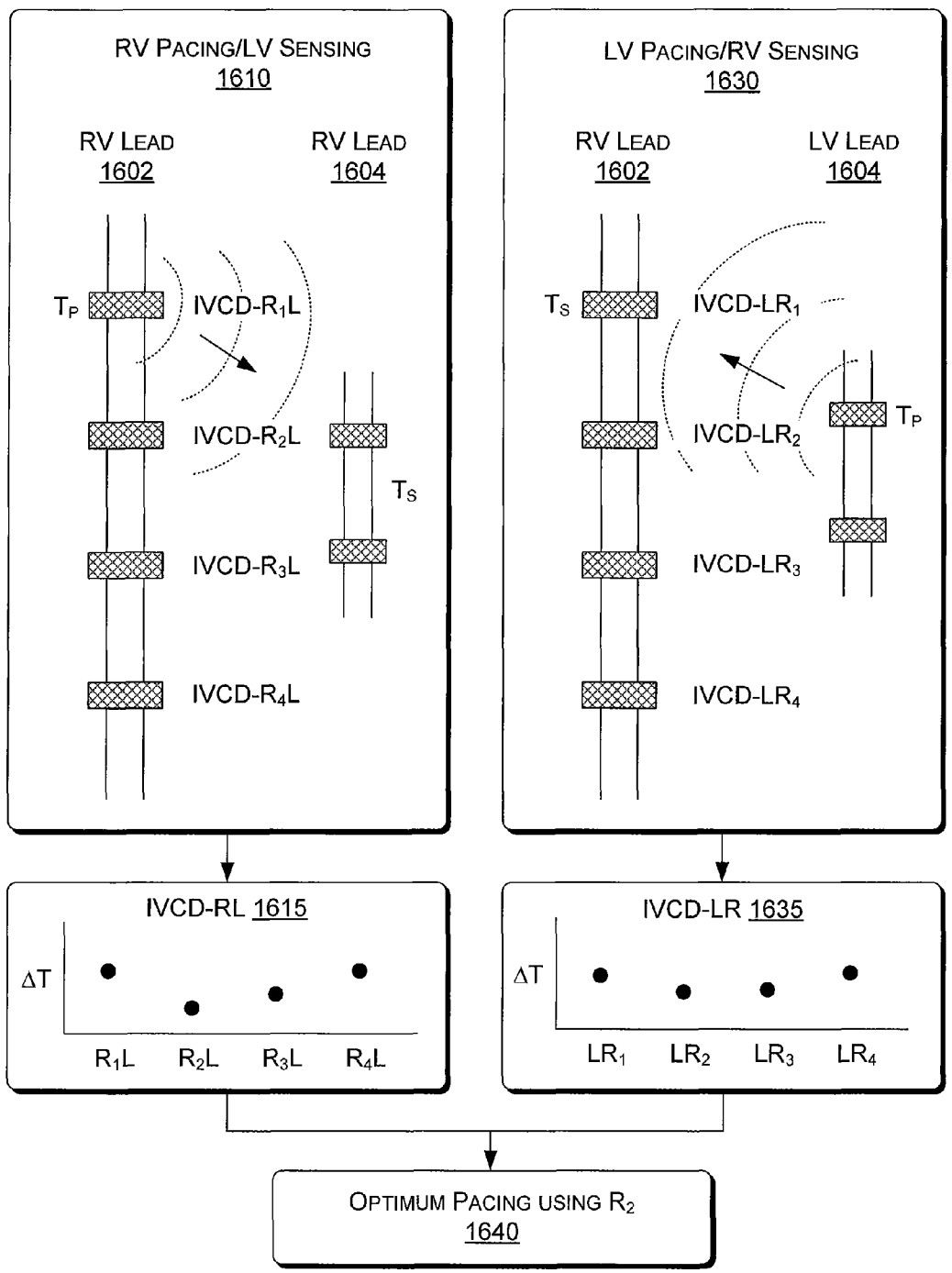
FIG. 16 is a diagram of a quadripolar right ventricular lead and a bipolar left ventricular lead and plots for interventricular conduction delays for use in selecting an optimum right ventricular lead electrode for right ventricular pacing.

FIG. 16 shows an exemplary method 1600 that includes use of a quadripolar right ventricular lead 1602 and a bipolar left ventricular lead 1604. In FIG. 16 a series of electrodes are associated with the right ventricle while in FIG. 4 a series of electrodes are associated with the left ventricle. In particular, the arrangements of FIG. 4 are more suited to a therapy that relies on LV pacing while the arrangements of FIG. 16 are more suited to a therapy that relies on RV pacing. As explained with respect to FIG. 17, a combination of the arrangements of FIG. 4 and FIG. 16 may be used. For example, an RV lead may include a series of electrodes and an LV lead may include a series of electrodes. In such an example, with respect to pacing/sensing, a variety of combinations are possible using one or more of the electrodes of the RV lead and one or more of the electrodes of the LV lead.

Referring again to the method 1600 of FIG. 16, an RV pacing and LV sensing block 1610 illustrates a wave front propagating from RV lead electrode $R_1$ (e.g., unipolar energy delivery) to the LV sensing electrodes (e.g., bipolar sensing); thus, corresponding to measurement of IVCD-$R_1$L. A LV pacing and RV sensing block 1630 illustrates a wave front propagating from the LV electrodes (e.g., bipolar energy delivery) to the RV lead electrode $R_1$ (e.g., unipolar sensing); thus, corresponding to measurement of IVCD-LR$_1$.

Plot 1615 shows IVCD-RL as a time delay ($\Delta$T) versus energy delivery/sensing configuration while plot 1635 shows IVCD-LR as a time delay ($\Delta$T) versus energy delivery/sensing configuration. The data of plots 1615 and 1635 may be used in a determination block 1640 to determine optimum electrode configuration for RV pacing. In the example of FIG. 16, single site pacing using RV lead electrode $R_2$ corresponds to the shortest interventricular conduction delay.

Figure 17:
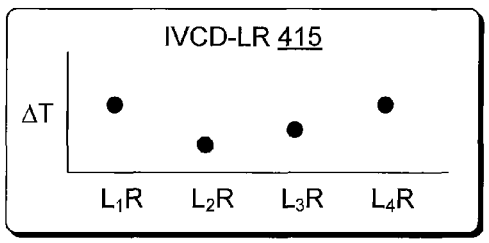
FIG. 17 is a diagram of various electrode combinations and corresponding plots that may be used to optimize electrode configuration for use in delivery of a cardiac stimulation therapy.
Figure 17:
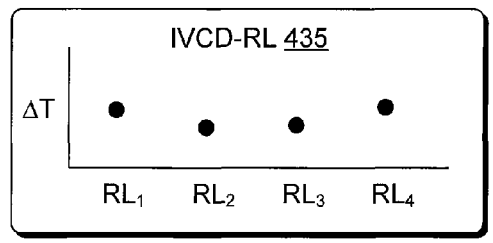
Figure 17:
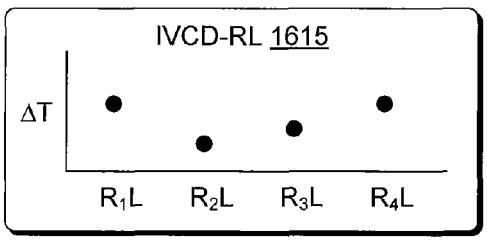
Figure 17:
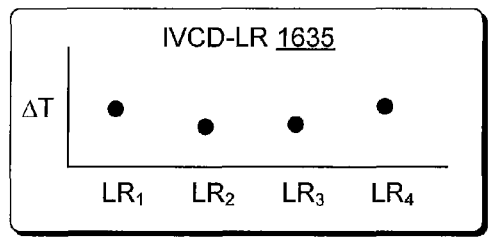
Figure 17:
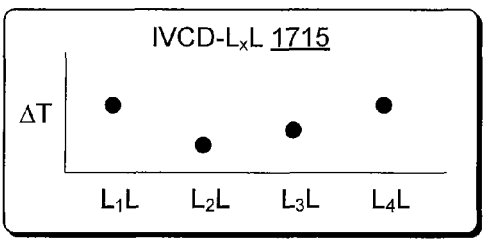
Figure 17:
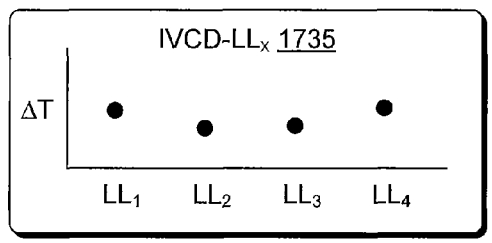
Figure 17:
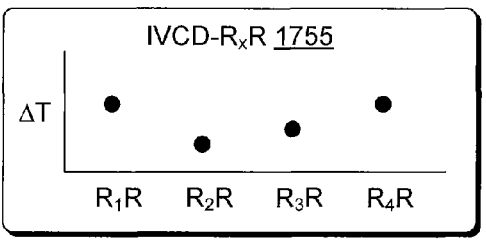
Figure 17:
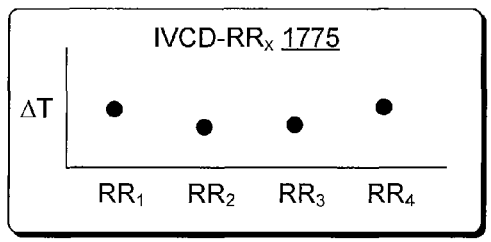

As already mentioned, FIG. 17 shows a variety of exemplary methods 1700 in the form of plots of time delay versus electrode configuration for a variety of electrode configurations. The plots 415 and 435 are the same as those presented in FIG. 4 and the plots 1615 and 1635 are the same as those presented in FIG. 16. Plot 1715 corresponds to data acquired via delivery of stimulation energy using a series of electrodes ($L_1$ through $L_4$) associated with the left ventricle and sensing with one or more other electrodes associated with the left ventricle. Plot 1735 corresponds to data acquired using a reversed arrangement for delivering energy and sensing. Plot 1755 corresponds to data acquired via delivery of stimulation energy using a series of electrodes ($R_1$ through $R_4$) associated with the right ventricle and sensing with one or more other electrodes associated with the right ventricle. Plot 1775 corresponds to data acquired using a reversed arrangement for delivering energy and sensing. Other arrangements are possible where such conduction information may be acquired and subsequently used to adjust or optimize delivery of therapy (see, e.g., the block 1212 of FIG. 12).

FIG. 18 shows a series of equations 1800 that may be used for atrial and/or ventricular pacing, including bi-ventricular pacing. As described herein, various techniques include adjusting one or more pacing parameters based at least in part on one or more conduction delays. Such techniques may use variables $\Delta$P (P wave width), $\Delta$A (A wave width), DD (end of P wave to point of QRS complex) and/or AD (end of A wave to point of QRS complex). Two parameters, $\delta$ and $\beta$, are discussed in more detail below. The parameter $\delta$ may depend on $\Delta$P or $\Delta$A while the parameter $\beta$ may depend on $\delta$ and DD or AD, as indicated by the following equations (Eqns. 1 and 2):

$$\delta = f(\Delta P) \text{ or } f(\Delta A) \quad (1)$$

$$\beta = \delta/DD \text{ or } \delta/AD \quad (2)$$

These parameters may be used to determine one or more pacing parameters, for example, as indicated by the following equations (Eqns. 3 and 4):

$$PV = \Delta P + \beta * DD \quad (3)$$

$$AV = \Delta A + \beta * AD \quad (4)$$

The PV or AV of Eqns. 3 and 4 may be used to determine an optimal PV or AV. These may depend on activity state of a patient, as indicated by the states block 1510 and the PV or AV states block 1820. For interventricular delay (VV), it may depend on activity and hence may change when activity state changes, as indicated by the VV states block 1830. While various activity states are shown in FIG. 15, a single state may be used where, in essence, the "AS" variable may be removed from the equations in blocks 1820 and 1830.

VV is used for bi-ventricular pacing and the following equations (Eqns. 5 and 6) may be used:

$$PV'' = PV' + VV \quad (5)$$

$$AV'' = AV' + VV \quad (6)$$

where PV' and AV' are for a master ventricle (paced first) and where PV" and AV" are for a slave ventricle (paced second).

According to the equations of FIG. 18, a general method pertains to pacing of a single ventricle (e.g., block 1820) while another general method pertains to bi-ventricular pacing (e.g., blocks 1820 and 1830). As indicated in block 1810, for purposes of generality, the subscript "x" is used to represent a particular activity state ($AS_x$) from a set of two or more activity states (e.g., $AS_0, AS_1, \ldots AS_N$).

As already mentioned, the state block 1810 defines various activity states. The activity states include a base state, for example, a rest state denoted by a subscript "0". In other examples, the subscript "rest" is used. The activity states include at least two states, for example, a base state and another activity state. In FIG. 18, the states range from the base state to activity state "N", which may be an integer without any numeric limitation (e.g., N may equal 5, 10, 100, 1000, etc.). The number of activity states may depend on patient condition and patient activity. For example, a patient that is bedridden may have few activity states when compared to a young patient (e.g., 40 years old) fitted with a pacemaker that leads an active life with a regular exercise regimen.

The PV or AV states block 1820 presents equations for the parameters β and δ as well as for a base state PV and AV and PV and AV for a state other than a base activity state, referred to as $AS_x$, where x=1, 2, ... N.

The VV states block 1830 presents equations for the parameters a, Δ and $\Delta_{IVCD}$ and VV for a base activity state ($AS_0$) and another activity state ($AS_x$). Theses equations may be used in various scenarios described herein.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
   measuring a plurality of interventricular conduction delays using left ventricular pacing and right ventricular sensing wherein each interventricular conduction delay (IVCD-LR) corresponds to a different electrode configuration for a left ventricular lead;
   measuring a plurality of interventricular conduction delays using right ventricular pacing and left ventricular sensing wherein each interventricular conduction delay (IVCD-RL) corresponds to a different electrode configuration for the left ventricular lead;
   determining the shortest conduction delay; and
   based on the shortest conduction delay, selecting an electrode configuration for the left ventricular lead for use in left ventricular pacing.

2. The method of claim 1 further comprising performing the method during implantation of a left ventricular lead.

3. The method of claim 2 further comprising positioning the left ventricular lead based on the shortest conduction delay.

4. The method of claim 1 wherein the determining the shortest conduction delay comprises averaging IVCD-LR and IVCD-RL values for each electrode configuration for the left ventricular lead.

5. The method of claim 1 wherein the selecting comprises selecting the electrode configuration that corresponds to the shortest IVCD-LR value.

6. The method of claim 1 wherein the electrode configurations for the left ventricular lead comprise one or more single site electrode configurations.

7. The method of claim 1 wherein the electrode configurations for the left ventricular lead comprise one or more multi-site electrode configurations.

8. The method of claim 1 wherein the electrode configurations for the left ventricular lead comprise one or more single site electrode configurations and one or more multi-site electrode configurations.

9. A method comprising:
   delivering a cardiac pacing therapy using left ventricular, single site pacing;
   measuring an interventricular conduction delay using the left ventricular, single site pacing and right ventricular sensing (IVCD-LR);
   measuring an interventricular conduction delay using right ventricular pacing and the left ventricular, single site for sensing (IVCD-RL);
   comparing the interventricular conduction delays to an interventricular conduction delay limit;
   deciding whether to select a different site for left ventricular, single site pacing if the interventricular conduction delays exceed the interventricular conduction delay limit.

10. The method of claim 9 wherein the limit comprises an optimal interventricular conduction delay value.

11. The method of claim 9 further comprising, if a different site is selected, measuring one or more interventricular conduction delays using the different site.

12. The method of claim 9 wherein the left ventricular, single site pacing uses an electrode configuration that comprises an electrode associated with a left ventricular lead.

13. The method of claim 9 wherein the left ventricular, single site pacing uses a case electrode of an implantable device.

14. The method of claim 9 wherein the left ventricular, single site pacing uses an electrode configuration that comprises two electrodes associated with a left ventricular lead.

15. The method of claim 9 wherein the left ventricular, single site pacing uses a unipolar electrode configuration.

16. The method of claim 9 wherein the left ventricular, single site pacing uses a bipolar electrode configuration.

17. A method comprising:
   measuring a plurality of interventricular conduction delays using right ventricular pacing and left ventricular sensing wherein each interventricular conduction delay (IVCD-RL) corresponds to a different electrode configuration for a right ventricular lead;
   measuring a plurality of interventricular conduction delays using left ventricular pacing and right ventricular sensing wherein each interventricular conduction delay (IVCD-LR) corresponds to a different electrode configuration for the right ventricular lead;
   determining the shortest conduction delay; and
   based on the shortest conduction delay, selecting an electrode configuration for the right ventricular lead for use in right ventricular pacing.

18. The method of claim 17 further comprising performing the method during implantation of a right ventricular lead.

19. The method of claim 17 wherein the determining the shortest conduction delay comprises averaging IVCD-RL and IVCD-LR values for each electrode configuration for the right ventricular lead.

20. The method of claim 17 wherein the selecting comprises selecting the electrode configuration that corresponds to the shortest IVCD-RL value.

21. The method of claim 17 wherein the electrode configurations for the right ventricular lead comprise one or more single site electrode configurations.

22. The method of claim 17 wherein the electrode configurations for the right ventricular lead comprise one or more multi-site electrode configurations.

23. The method of claim 17 wherein the electrode configurations for the right ventricular lead comprise one or more single site electrode configurations and one or more multi-site electrode configurations.

* * * * *